United States Patent
Yang et al.

(10) Patent No.: US 8,980,887 B2
(45) Date of Patent: Mar. 17, 2015

(54) 2-ARYL IMIDAZO[1,2-A]PYRIDINE-3-ACETAMIDE DERIVATIVES, PREPARATION METHODS AND USES THEREOF

(75) Inventors: Rifang Yang, Beijing (CN); Yunfeng Li, Beijing (CN); Yongzhen Li, Beijing (CN); Nan Zhao, Beijing (CN); Liuhong Yun, Beijing (CN); Juanjuan Qin, Beijing (CN); Zhongyao Feng, Beijing (CN); Youzhi Zhang, Beijing (CN)

(73) Assignees: Institute of Pharmacology, Beijing (CN); Toxicology Academy of Military Medical Sciences P.L.A., China, Beijing (CN)

( * ) Notice: Subject to any disclaimer, the term of this patent is extended or adjusted under 35 U.S.C. 154(b) by 0 days.

(21) Appl. No.: 13/805,967

(22) PCT Filed: Jun. 9, 2011

(86) PCT No.: PCT/CN2011/075500
§ 371 (c)(1),
(2), (4) Date: Apr. 18, 2013

(87) PCT Pub. No.: WO2011/160548
PCT Pub. Date: Dec. 29, 2011

(65) Prior Publication Data
US 2013/0203754 A1    Aug. 8, 2013

(30) Foreign Application Priority Data

Jun. 25, 2010   (CN) .......................... 2010 1 0209752

(51) Int. Cl.
*A61K 31/535* (2006.01)
*C07D 471/04* (2006.01)

(52) U.S. Cl.
CPC .................... *C07D 471/04* (2013.01)
USPC ........ 514/233.2; 514/300; 435/375; 546/121; 544/127

(58) Field of Classification Search
USPC ................ 514/233.2, 300; 435/375; 546/121; 544/127
See application file for complete search history.

(56) References Cited

FOREIGN PATENT DOCUMENTS

| CN | 1858050 A | 11/2006 |
|---|---|---|
| CN | 101336242 A | 12/2008 |
| WO | WO 99/51594 | 10/1999 |
| WO | WO 2008022396 A1 * | 2/2008 |

OTHER PUBLICATIONS

STN Accession No. 2006:1186013 CAPLUS, 2006.*

Trapani et al, J. Med. Chem. 2005, 48, 292-305.*
Supplementary European Search Report dated Oct. 23, 2013 PCT/CN2011075500 in corresponding application.
S. Paul, et al., "Zinc Medicated Friedel-Crafts Acylation in Solvent-Free Conditions Under Microwave Irradiation" Synthesis 2003, No. 18, pp. 2877-2881.
G. Trapani, et al., Structure-Activity Relationships and Effects on Neuroactive Steroid Synthesis in a Series of 2-Phenylimidazo[1,2-α] Pyridineacetamide Peripheral Benzodiazepine Receptors Ligands, Journal of Medicinal Chemistry, 2005, vol. 48, No. 1, Published Dec. 13, 2004, pp. 292-305.
Papadopoulos V. et al., "Translocator protein (18kDa): new nomenclature for the peripheral-type benzodiazepine receptor based on its structure and molecular function," *Trends in Pharmacological Science*, vol. 27, No. 8, p. 402-409 (2006).
Scarf A.M. et al., "The translocator protein (18 kDa): central nervous system disease and drug design," *Journal of Medicinal Chemistry*, vol. 52, No. 3, p. 581-592 (2009).
Li Y. et al., Synthesis and anxiolytic effects of 2-aryl imidazo[1,2-a] pyridine-3-acetamide derivatives, *Journal of International Pharmaceutical Research*, vol. 37, No. 4, p. 292-301 (2010).
James M.L. et al., "Development of ligands for the peripheral benzodiapene receptor," *Current Medicinal Chemistry*, vol. 13, No. 17, p. 1991-2001 (2006).
Samanta S. et al. "Search for Structural Requirements of 2-Phenylimidazo[1,2-α]pyridineacetamide Analogs to Improve Affinity and Selectivity towards Central and/or Peripheral Benzodiazepine Receptors," *Internet Electronic Journal of Molecular Design*, vol. 6, issue 7, p. 183-189 (2007).
Taliani S. et al. "Translocator protein ligands as promising therapeutic tools for anxiety disorders," *Current Medicinal Chemistry*, vol. 16, No. 26, p. 3359-3380 (2009).
Rupprecht R. et al. "Translocator protein (18 kD) as target for anxiolytics without benzodiazepine-like side effects," *Science* vol. 325, p. 490-495 (2009).

(Continued)

*Primary Examiner* — Wu-Cheng Winston Shen
*Assistant Examiner* — Jean Cornet
(74) *Attorney, Agent, or Firm* — Brinks Gilson & Lione

(57) ABSTRACT

Disclosed are 2-arylimidazo[1,2-a]pyridine-3-acetamide derivatives represented by formula I, their tautomer, racemate or optical isomer, their pharmaceutically acceptable salt, or their solvates, wherein $R^1$, $R^2$, $R^3$ and $R^4$ are defined as in the specification. Preparation methods of said compounds and use of said compounds in treating and/or preventing central nervous system disease associated with TSPO functional disorder

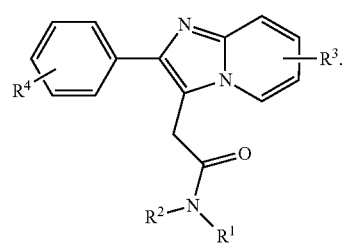

19 Claims, 6 Drawing Sheets

(56) References Cited

OTHER PUBLICATIONS

Kita A. et al., "Lack of tolerance to anxiolysis and withdrawal symptoms in mice repeatedly treated with AC-5216, a selective TSPO ligand," *Progress in Neuro-Psychopharmacology and Biological Psychiatry*, vol. 33, p. 1040-1045 (2009).

Notification of Reexamination of Chinese Application No. 201010209752.0—With English translation.

G. Trapani, et al., "Synthesis and Binding Affinity of 2-Phenylimidazo [1,2- a] pyridine Derivatives for both Central and Peripheral Benzodiazepine Receptors. A New Series of High-Affinity and Selective Ligands for the Peripheral Type", J. Med. Chem. 1997, vol. 40, pp. 3109-3118.

Y. Sumalatha, et al., "Synthesis and Spectral Characterization of Process-Related Substances to the Hypnotic Agent Zolpidem", ARKAT USA, Inc., ARKIVOC-2009 (vii), pp. 143-149.

\* cited by examiner

2-ARYL IMIDAZO[1,2-A]PYRIDINE-3-ACETAMIDE DERIVATIVES, PREPARATION METHODS AND USES THEREOF

CROSS-REFERENCE TO RELATED APPLICATIONS

The present application is a §371 national stage application of PCT International Application No. PCT/CN2011/075500, filed Jun. 9, 2011, which application claims a right of priority to Chinese Patent Application No. 201010209752.0, filed Jun. 25, 2010, both of which are incorporated herein by reference in their entirety.

TECHNICAL FIELD

The present invention belongs to medical chemical field, and relates to 2-arylimidazo[1,2-a]pyridine-3-acetamide derivatives, their preparation methods and uses. The present invention further relates to a pharmaceutical composition comprising a compound of Formula I, its tautomer, its racemic or optical isomer, its pharmaceutically acceptable salt, or its solvate, a method for treatment and/or prophylaxis of a central nervous system disease associated with TSPO functional disorder, and a method for combating cell apoptosis in vivo or in vitro, combating a tumor, inflammatory immunoregulation, neuroprotection, or regulating TSPO activity.

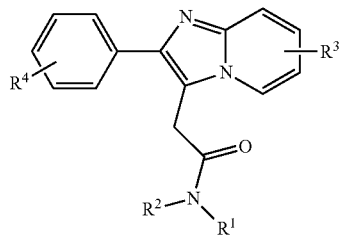

Formula I

BACKGROUND ART

Anxiety disorder has main symptoms such as panic, uneasy and repeated anxieties, and patients under mental disorder state cannot exert normal living ability and effectively work, and long-term of diseases may grievously influence patients' health and daily life, and even may induce more serious consequences such as suicide. In addition, the later phase of anxiety is usually accompanied with depression symptoms. Some statistical results show that the patients with anxiety are of 8-13% of the world population, and most of them are lack of necessary medicinal intervention and treatment. Hence, it is very important to develop medicaments with good activity against anxiety and depression.

Traditional drugs such as diazepam, alpidem are widely used in clinic for treatment of anxiety and depression, but these previous drugs can not only act on peripheral benzodiazepine receptor (PBR), but also act on central benzodiazepine receptor (CBR), so that they may frequently induce side effects such as sedation, hypnosis, amnesia, muscle relaxation, tolerance, and may easily induce drug dependence and addiction. Thus, it is urgent to have anxiolytics drugs with higher target specificity, less side effects and lower drug dependence.

Some researches show that PBR is mainly on cell mitochondrial membrane, and is one of pivotal components of cell mitochondrial membrane receptor complex, and thus is also called as mitochondrial benzodiazepine receptor (MBR). The whole structure of the receptor complex comprises a translocator protein 18 KDa (TSPO) located at mitochondrial outer membrane, and TSPO as the minimum functional unit of PBR/MBR can combine with pharmaceutical ligand and cholesterol and exert important functions (*Trends Pharmacol Sci*, 2006, 27(8): 402-409; *J Med Chem*, 2009, 52(3): 581-592.).

TSPO has potential value in treatment of anxiety. After TSPO combines with corresponding ligand, it can promote the entrance of cholesterol into mitochondria, and stimulate biosynthesis of neurosteroids, while neurosteroids can act on GABA-A receptor and produce anxiolytic effects, but do not produce apparent side effects.

At present, TSPO ligands are very widely studied, and it has been reported that many compounds exert good activity in vivo and in vitro, and TSPO ligands having relatively high affinity and selectivity are reported as well. According to their chemical structure, there are mainly benzodiazepines (e.g., 4'-chlorodiazepam (Ro5-4864)], isoquinoline amides, benzothiazepines, benzoxazepines, indole acetamides (e.g., FGIN), imidazopyridine acetamides, aryloxyaniline derivatives, pyrazolopyrimidine acetamides, 3-indolyloxamides, 2-arylpyrimidine derivatives, and 2-aryl-8-oxypurine derivatives. These ligands have roughly same basic structure, and can be concluded as: containing one hydrogen bond donator (δ1, usually amide), two lipophilic areas (PAR and FRA) on mother ring backbone, and another lipophilic area (LA) binding to receptor via allosterism (*Curr Med Chem*, 2006, 13(17): 1991-2001; *Curr Med Chem*, 2009, 16(26): 3359-3380.).

In corresponding animal models and clinical studies, some of the selective TSPO ligands had been showed potential values in creating new drugs with TSPO as target. For example, PK11195, a TSPO/PBR selective antagonist, has been widely used in finding new types of TSPO ligands and activity comparison as a tool drug. In addition, Emapunil (AC-5216, XBD173) has high selectivity and affinity, less side effects, no remarkable withdrawal symptoms and drug withdraw rebounding symptoms, and thus enters phase II clinical research (Science 2009, 325, 490-195; *Prog Neuro-Psychoph*, 2009, 33, 1040-1045.). However, most of these compounds have poor pharmacokinetics, low bioavailability, difficulty in penetrating blood brain barrier. Hence, it is still needed to find better TSPO ligands.

CONTENTS OF THE INVENTION

One aspect of the present invention relates to a compound of Formula I, its tautomer, its racemic or optical isomer, its pharmaceutically acceptable salt (a salt acceptable in pharmacy, which is water soluble), or its solvate,

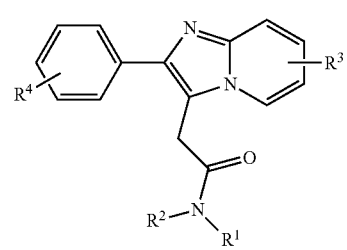

I wherein:
$R^1$ is selected from ethyl, propyl, butyl, and methoxyethyl;
$R^2$ is selected from benzyl, 2-pyridinylmethyl, 3-pyridinylmethyl, 4-pyridinylmethyl, 2-morpholinylethyl, and 3-morpholinylpropyl;

R³, R⁴ are independently selected from H, halogen, alkyl, substituted hydrocarbonyl, alkenyl, substituted alkenyl, phenyl, substituted phenyl, heteroaryl, substituted heteroaryl, $C_1$-$C_6$ alkoxyl, $C_5$-$C_{10}$ aryloxy, substituted aryloxy, $C_1$-$C_6$ alkylamino, $C_5$-$C_{10}$ arylamino, substituted arylamino, di-($C_1$-$C_6$ alkyl)amino, di-($C_5$-$C_{10}$ aryl)amino, di-(substituted aryl)amino, $C_{1-10}$ hydrocarbonylacyloxy, $C_{6-10}$ arylacyloxy, $C_{1-10}$ hydrocarbonylacylamino, $C_{6-10}$ arylacylamino, carboxyl, $C_{1-10}$ hydrocarbonyloxyformyl, $C_{6-10}$ aryloxyformyl, aminoformyl, $C_{1-10}$ hydrocarbonylaminoformyl, or $C_{6-10}$ arylaminoformyl; wherein the heteroaromatic cycle is a monocyclic or fused aromatic hydrocarbonyl having 1-3 heteroatoms selected from N, O or S, each of the substituents of groups having substituents is selected from halogen, hydroxyl, cyano, nitro, $C_{1-6}$ alkyl, $C_{1-6}$ alkoxyl, $C_{1-6}$ alkylthio, mono- or di- or tri-halogenated $C_{1-6}$ alkyl, amino, $C_{1-6}$ alkylamino, $C_{1-10}$ hydrocarbonylacyloxy, $C_{1-10}$ hydrocarbonylacylamino, $C_{6-10}$ arylacyloxy, and $C_{6-10}$ arylacylamino.

According to the present invention, the pharmaceutically salt of the compound of Formula I can be an acid addition salt or a salt formed with an alkali. The acid addition salt can be an inorganic acid salt, including but not being limited to hydrochloride, sulfate, phosphate, or hydrobromide, etc.; or an organic acid salt, including but not being limited to acetate, oxalate, citrate, gluconate, succinate, tartrate, p-tosylate, mesylate, benzoate, lactate, or maleate, etc.; the salt of the compound of Formula I formed with an alkali can be an alkali metal salt, including but not being limited to lithium salt, sodium slat, or potassium salt; or an alkaline earth metal salt, including but not being limited to calcium salt or magnesium salt; or an organic alkali base, including but not being limited to diethanolamine salt or choline salt, etc.; or a chiral alkali salt, including but not being limited to alkylphenylamine salt, etc.

The solvate of the compound of the present invention can be a hydrate, and optionally comprises other crystallization solvents such as alcohols, including but not being limited to ethanol.

According to the present invention, the compound of Formula I can be present in cis/trans isomers, and the present invention relates to cis-form and trans-form and a mixture of these forms. If necessary, the preparation of single stereoisomer can be performed by resolution of mixture according to conventional methods, or by stereo-selective synthesis. If there is a mobile hydrogen atom, the present invention can also relate to the tautomers of the compound of Formula I.

In one embodiment of the present invention, R³ has 1-2 substituents, and R³ is at 4-, 5-, 6-, or 7-position of imidazo[1,2-a]pyridine ring; R⁴ has 1-3 substituents, and R⁴ is at o-, m- or p-position of benzene ring.

In one embodiment of the present invention, R³, R⁴ are independently selected from F, Cl, Br, I, $C_1$-$C_6$ alkyl, $C_1$-$C_3$ alkoxylethyl, and $C_1$-$C_6$ alkoxyl.

In one embodiment of the present invention, R³, R⁴ are independently selected from F, Cl, Br, $C_1$-$C_4$ alkyl, and $C_1$-$C_4$ alkoxyl.

In one embodiment of the present invention, R³, R⁴ are independently selected from F, Cl, methyl, ethyl, methoxyethyl, methoxy, and ethoxy.

In one embodiment of the present invention, the compound of Formula I, its tautomer, its racemic or optical isomer, its pharmaceutically acceptable salt, or its solvate, respectively meet one more of following items (1) to (4):
(1) R¹ is ethyl or methoxyethyl;
(2) R² is benzyl, 2-pyridinylmethyl, 3-pyridinylmethyl, 4-pyridinylmethyl, or 2-morpholinylethyl;
(3) R³ is 6-methyl or 7-methyl;
(4) R⁴ is 4-chloro, 3,4-dichloro, 4-methyl, or 4-methoxy.

In one embodiment of the present invention, the compound of Formula I, its tautomer, its racemic or optical isomer, its pharmaceutically acceptable salt, or its solvate, is selected from the following Compounds 1-28:

N-benzyl-N-ethyl-2-(4-chlorophenyl)-7-methylimidazo[1,2-a]pyridine-3-acetamide;

N-ethyl-N-(2-pyridinylmethyl)-2-(4-chlorophenyl)-7-methylimidazo[1,2-a]pyridine-3-acetamide.hydrochloride;

N-ethyl-N-(3-pyridinylmethyl)-2-(4-chlorophenyl)-7-methylimidazo[1,2-a]pyridine-3-acetamide.hydrochloride;

N-ethyl-N-(4-pyridinylmethyl)-2-(4-chlorophenyl)-7-methylimidazo[1,2-a]pyridine-3-acetamide.hydrochloride;

N-(2-methoxyethyl)-N-(2-pyridinylmethyl)-2-(4-chlorophenyl)-7-methylimidazo[1,2-a]pyridine-3-acetamide.hydrochloride;

N-(2-methoxyethyl)-N-(3-pyridinylmethyl)-2-(4-methylphenyl)-7-methylimidazo[1,2-a]pyridine-3-acetamide.hydrochloride;

N-benzyl-N-ethyl-2-(3,4-dichlorophenyl)-7-methylimidazo[1,2-a]pyridine-3-acetamide;

N-ethyl-N-(2-pyridinylmethyl)-2-(3,4-dichlorophenyl)-7-methylimidazo[1,2-a]pyridine-3-acetamide.hydrochloride;

N-ethyl-N-(3-pyridinylmethyl)-2-(3,4-dichlorophenyl)-7-methylimidazo[1,2-a]pyridine-3-acetamide.hydrochloride;

N-ethyl-N-(4-pyridinylmethyl)-2-(3,4-dichlorophenyl)-7-methylimidazo[1,2-a]pyridine-3-acetamide.hydrochloride;

N-(2-methoxyethyl)-N-(2-pyridinylmethyl)-2-(3,4-dichlorophenyl)-7-methylimidazo[1,2-a]pyridine-3-acetamide.hydrochloride;

N-(2-methoxyethyl)-N-(3-pyridinylmethyl)-2-(3,4-dichlorophenyl)-7-methylimidazo[1,2-a]pyridine-3-acetamide.hydrochloride;

N-benzyl-N-ethyl-2-(4-methylphenyl)-7-methylimidazo[1,2-a]pyridine-3-acetamide;

N-ethyl-N-(2-pyridinylmethyl)-2-(4-methylphenyl)-7-methylimidazo[1,2-a]pyridine-3-acetamide.hydrochloride;

N-ethyl-N-(3-pyridinylmethyl)-2-(4-methylphenyl)-7-methylimidazo[1,2-a]pyridine-3-acetamide.hydrochloride;

N-ethyl-N-(4-pyridinylmethyl)-2-(4-methylphenyl)-7-methylimidazo[1,2-a]pyridine-3-acetamide.hydrochloride;

N-(2-methoxyethyl)-N-(2-pyridinylmethyl)-2-(4-methylphenyl)-7-methylimidazo[1,2-a]pyridine-3-acetamide.hydrochloride;

N-(2-methoxyethyl)-N-(3-pyridinylmethyl)-2-(4-methylphenyl)-7-methylimidazo[1,2-a]pyridine-3-acetamide.hydrochloride;

N-benzyl-N-ethyl-2-(4-methoxyphenyl)-7-methylimidazo[1,2-a]pyridine-3-acetamide;

N-ethyl-N-(2-pyridinylmethyl)-2-(4-methoxyphenyl)-7-methylimidazo[1,2-a]pyridine-3-acetamide.hydrochloride;

N-ethyl-N-(3-pyridinylmethyl)-2-(4-methoxyphenyl)-7-methylimidazo[1,2-a]pyridine-3-acetamide.hydrochloride;

N-ethyl-N-(4-pyridinylmethyl)-2-(4-methoxyphenyl)-7-methylimidazo[1,2-a]pyridine-3-acetamide.hydrochloride;

N-(2-methoxyethyl)-N-(2-pyridinylmethyl)-2-(4-methoxyphenyl)-7-methylimidazo[1,2-a]pyridine-3-acetamide.hydrochloride;

N-(2-methoxyethyl)-N-(3-pyridinylmethyl)-2-(4-methoxyphenyl )-7-methylimidazo[1,2-a]pyridine-3-acetamide.hydrochloride;

N-(2-methoxyethyl)-N-(2-morpholinylethyl)-2-(4-methylphenyl)-7-methylimidazo[1,2-a]pyridine-3-acetamide.hydrochloride;

N-(2-methoxyethyl)-N-(2-morpholinylethyl)-2-(4-methylphenyl)-6-methylimidazo[1,2-a]pyridine-3-acetamide.hydrochloride;

N-ethyl-N-(4-pyridinylmethyl)-2-(4-methylphenyl)-6-methylimidazo[1,2-a]pyridine-3-acetamide.hydrochloride; and N-ethyl-N-(4-pyridinylmethyl)-2-(4-chlorophenyl)-6-methylimidazo[1,2-a]pyridine-3-acetamide.hydrochloride.

The structural formulas of the above Compounds 1-28 are shown in Table 1:

TABLE 1

| | Structural formulas of Compound 1-28 (as prepared in Example 13-40) | |
|---|---|---|
| No | Compound name | Structural formula |
| 1 | N-benzyl-N-ethyl-2-(4-chlorophenyl)-7-methylimidazo[1,2-a]pyridine-3-acetamide | |
| 2 | N-ethyl-N-(2-pyridinylmethyl)-2-(4-chlorophenyl)-7-methylimidazo[1,2-a]pyridine-3-acetamide•hydrochloride | |
| 3 | N-ethyl-N-(3-pyridinylmethyl)-2-(4-chlorophenyl)-7-methylimidazo[1,2-a]pyridine-3-acetamide•hydrochloride | |
| 4 | N-ethyl-N-(4-pyridinylmethyl)-2-(4-chlorophenyl)-7-methylimidazo[1,2-a]pyridine-3-acetamide•hydrochloride | |

TABLE 1-continued

Structural formulas of Compound 1-28 (as prepared in Example 13-40)

| No | Compound name | Structural formula |
|----|---------------|---------------------|
| 5 | N-(2-methoxyethyl)-N-(2-pyridinylmethyl)-2-(4-chlorophenyl)-7-methylimidazo[1,2-a]pyridine-3-acetamide•hydrochloride | 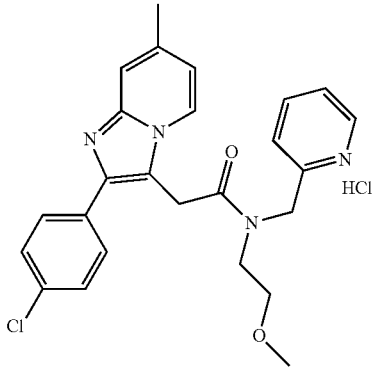 [SMILES: COCCN(Cc1ccccn1)C(=O)Cc1c(-c2ccc(Cl)cc2)nc2cc(C)ccn12 ; Cl] |
| 6 | N-(2-methoxyethyl)-N-(3-pyridinylmethyl)-2-(4-methylphenyl)-7-methylimidazo[1,2-a]pyridine-3-acetamide•hydrochloride | 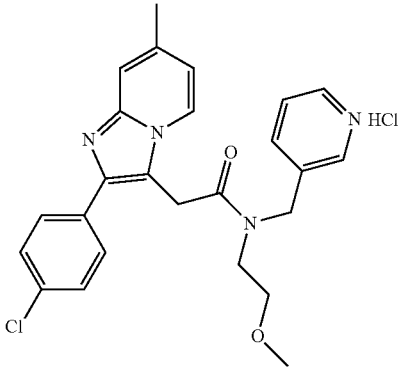 [SMILES: COCCN(Cc1cccnc1)C(=O)Cc1c(-c2ccc(Cl)cc2)nc2cc(C)ccn12 ; Cl] |
| 7 | N-benzyl-N-ethyl-2-(3,4-dichlorophenyl)-7-methylimidazo[1,2-a]pyridine-3-acetamide | 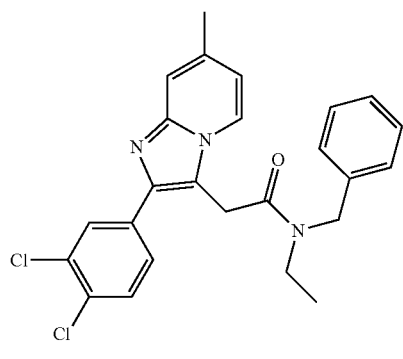 [SMILES: CCN(Cc1ccccc1)C(=O)Cc1c(-c2ccc(Cl)c(Cl)c2)nc2cc(C)ccn12] |
| 8 | N-ethyl-N-(2-pyridinylmethyl)-2-(3,4-dichlorophenyl)-7-methylimidazo[1,2-a]pyridine-3-acetamide•hydrochloride | 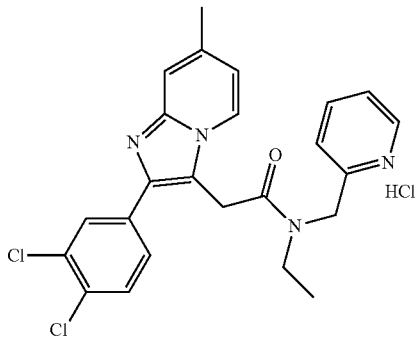 [SMILES: CCN(Cc1ccccn1)C(=O)Cc1c(-c2ccc(Cl)c(Cl)c2)nc2cc(C)ccn12 ; Cl] |

TABLE 1-continued

Structural formulas of Compound 1-28 (as prepared in Example 13-40)

| No | Compound name | Structural formula |
|---|---|---|
| 9 | N-ethyl-N-(3-pyridinylmethyl)-2-(3,4-dichlorophenyl)-7-methylimidazo[1,2-a]pyridine-3-acetamide•hydrochloride | 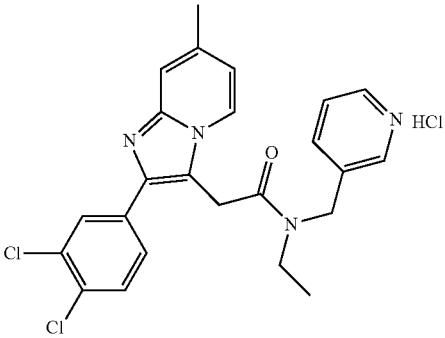 [SMILES: CCN(Cc1cccnc1)C(=O)Cc1c(-c2ccc(Cl)c(Cl)c2)nc2cc(C)ccn12 ; Cl] |
| 10 | N-ethyl-N-(4-pyridinylmethyl)-2-(3,4-dichlorophenyl)-7-methylimidazo[1,2-a]pyridine-3-acetamide•hydrochloride | 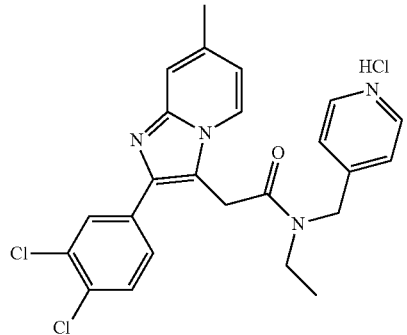 [SMILES: CCN(Cc1ccncc1)C(=O)Cc1c(-c2ccc(Cl)c(Cl)c2)nc2cc(C)ccn12 ; Cl] |
| 11 | N-(2-methoxyethyl)-N-(2-pyridinylmethyl)-2-(3,4-dichlorophenyl)-7-methylimidazo[1,2-a]pyridine-3-acetamide•hydrochloride | 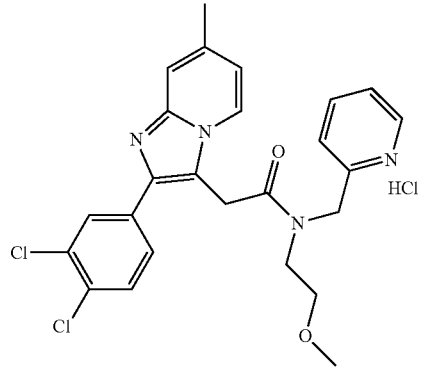 [SMILES: COCCN(Cc1ccccn1)C(=O)Cc1c(-c2ccc(Cl)c(Cl)c2)nc2cc(C)ccn12 ; Cl] |
| 12 | N-(2-methoxyethyl)-N-(3-pyridinylmethyl)-2-(3,4-dichlorophenyl)-7-methylimidazo[1,2-a]pyridine-3-acetamide•hydrochloride | 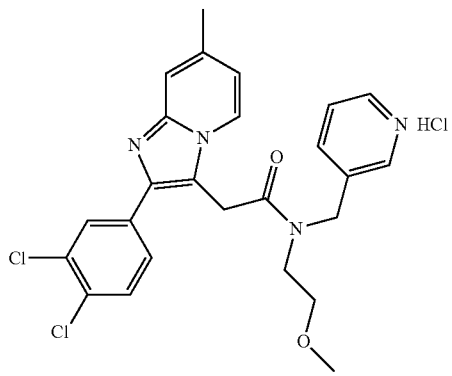 [SMILES: COCCN(Cc1cccnc1)C(=O)Cc1c(-c2ccc(Cl)c(Cl)c2)nc2cc(C)ccn12 ; Cl] |

TABLE 1-continued

Structural formulas of Compound 1-28 (as prepared in Example 13-40)

| No | Compound name | Structural formula |
|----|---------------|--------------------|
| 13 | N-benzyl-N-ethyl-2-(4-methylphenyl)-7-methylimidazo[1,2-a]pyridine-3-acetamide | 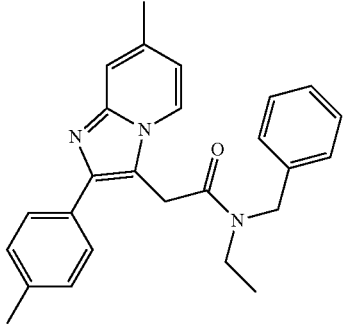 [SMILES: CCN(Cc1ccccc1)C(=O)Cc1c(-c2ccc(C)cc2)nc2cc(C)ccn12] |
| 14 | N-ethyl-N-(2-pyridinylmethyl)-2-(2-(4-methylphenyl)-7-methylimidazo[1,2-a]pyridino-3-acetamide•hydrochloride | 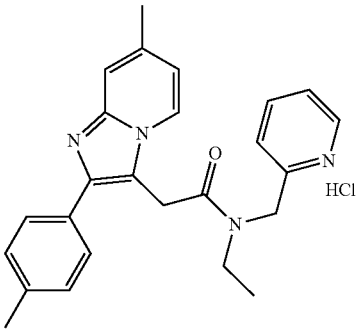 [SMILES: CCN(Cc1ccccn1)C(=O)Cc1c(-c2ccc(C)cc2)nc2cc(C)ccn12 ; Cl] |
| 15 | N-ethyl-N-(3-pyridinylmethyl)-2-(4-methylphenyl)-7-methylimidazo[1,2-a]pyridine-3-acetamide•hydrochloride | 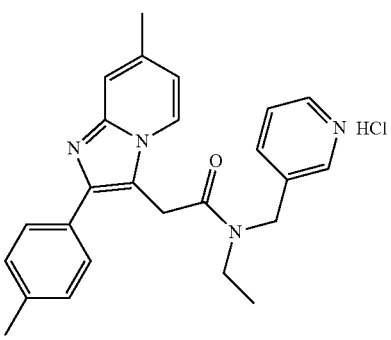 [SMILES: CCN(Cc1cccnc1)C(=O)Cc1c(-c2ccc(C)cc2)nc2cc(C)ccn12 ; Cl] |
| 16 | N-ethyl-N-(4-pyridinylmethyl)-2-(4-methylphenyl)-7-methylimidazo[1,2-a]pyridine-3-acetamide•hydrochloride | 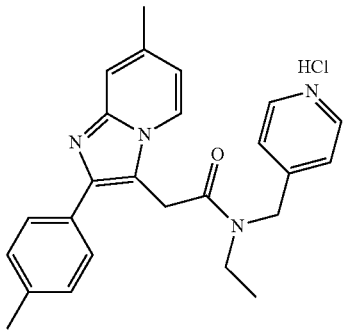 [SMILES: CCN(Cc1ccncc1)C(=O)Cc1c(-c2ccc(C)cc2)nc2cc(C)ccn12 ; Cl] |

TABLE 1-continued

Structural formulas of Compound 1-28 (as prepared in Example 13-40)

| No | Compound name | Structural formula |
|---|---|---|
| 17 | N-(2-methoxyethyl)-N-(2-pyridinylmethyl)-2-(4-methylphenyl)-7-methylimidazo[1,2-a]pyridine-3-acetamide•hydrochloride | 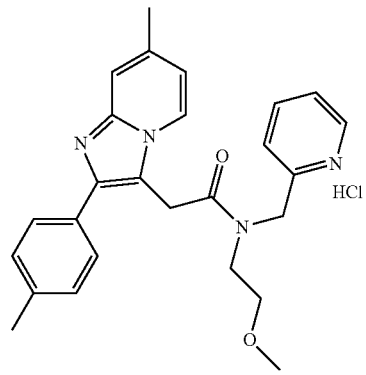 [SMILES: COCCN(Cc1ccccn1)C(=O)Cc1c(-c2ccc(C)cc2)nc2cc(C)ccn12 ; Cl] |
| 18 | N-(2-methoxyethyl)-N-(3-pyridinylmethyl)-2-(4-methylphenyl)-7-methylimidazo[1,2-a]pyridine-3-acetamide•hydrochloride | 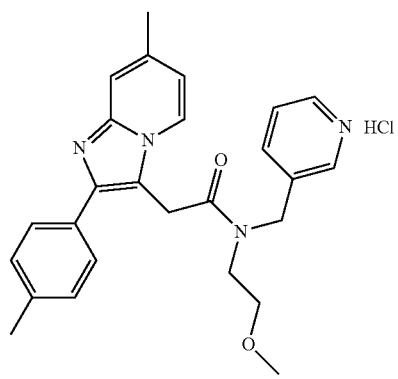 [SMILES: COCCN(Cc1cccnc1)C(=O)Cc1c(-c2ccc(C)cc2)nc2cc(C)ccn12 ; Cl] |
| 19 | N-benzyl-N-ethyl-2-(4-methoxyphenyl)-7-methylimidazo[1,2-a]pyridine-3-acetamide | 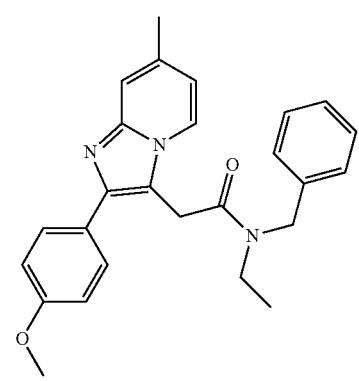 [SMILES: CCN(Cc1ccccc1)C(=O)Cc1c(-c2ccc(OC)cc2)nc2cc(C)ccn12] |
| 20 | N-ethyl-N-(2-pyridinylmethyl)-2-(4-methoxyphenyl)-7-methylimidazo[1,2-a]pyridine-3-acetamide•hydrochloride | 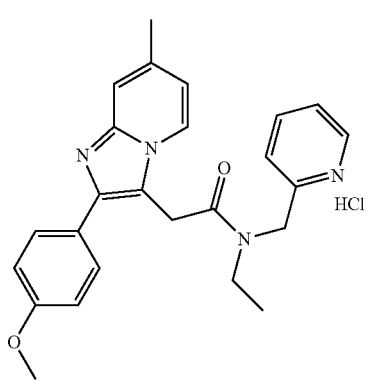 [SMILES: CCN(Cc1ccccn1)C(=O)Cc1c(-c2ccc(OC)cc2)nc2cc(C)ccn12 ; Cl] |

TABLE 1-continued

Structural formulas of Compound 1-28 (as prepared in Example 13-40)

| No | Compound name | Structural formula |
|----|---------------|--------------------|
| 21 | N-ethyl-N-(3-pyridinylmethyl)-2-(4-methoxyphenyl)-7-methylimidazo[1,2-a]pyridine-3-acetamide•hydrochloride | 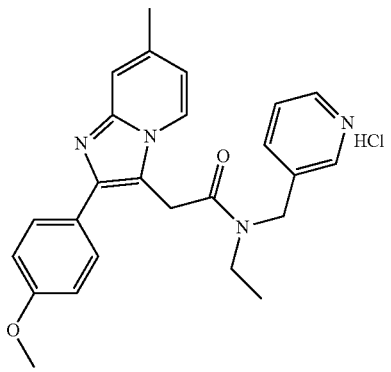 [SMILES: CCN(Cc1cccnc1)C(=O)Cc1c(-c2ccc(OC)cc2)nc2cc(C)ccn12 ; Cl] |
| 22 | N-ethyl-N-(4-pyridinylmethyl)-2-(4-methoxyphenyl)-7-methylimidazo[1,2-a]pyridine-3-acetamide•hydrochloride | 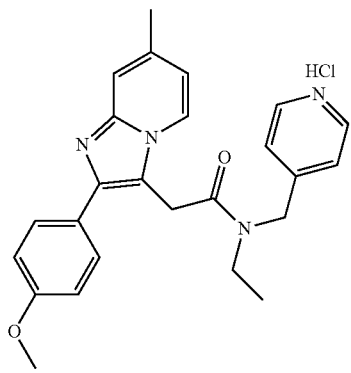 [SMILES: CCN(Cc1ccncc1)C(=O)Cc1c(-c2ccc(OC)cc2)nc2cc(C)ccn12 ; Cl] |
| 23 | N-(2-methoxyethyl)-N-(2-pyridinylmethyl)-2-(4-methoxyphenyl)-7-methylimidazo[1,2-a]pyridine-3-acetamide•hydrochloride | 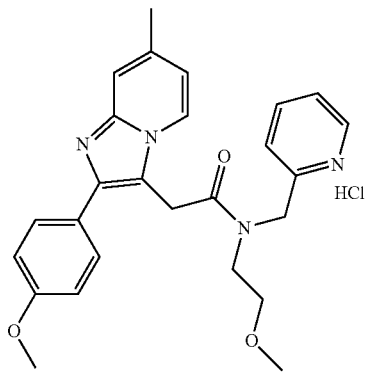 [SMILES: COCCN(Cc1ccccn1)C(=O)Cc1c(-c2ccc(OC)cc2)nc2cc(C)ccn12 ; Cl] |
| 24 | N-(2-methoxyethyl)-N-(3-pyridinylmethyl)-2-(4-methoxyphenyl)-7-methylimidazo[1,2-a]pyridine-3-acetamide•hydrochloride | 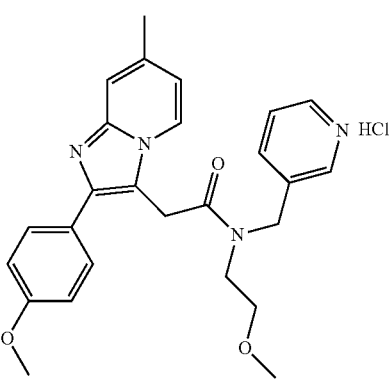 [SMILES: COCCN(Cc1cccnc1)C(=O)Cc1c(-c2ccc(OC)cc2)nc2cc(C)ccn12 ; Cl] |

TABLE 1-continued

Structural formulas of Compound 1-28 (as prepared in Example 13-40)

| No | Compound name | Structural formula |
| --- | --- | --- |
| 25 | N-(2-methoxyethyl)-N-(2-morpholinylethyl)-2-(4-methylphenyl)-7-methylimidazo[1,2-a]pyridine-3-acetamide•hydrochloride | |
| 26 | N-(2-methoxyethyl)-N-(2-morpholinylethyl)-2-(4-methylphenyl)-6-methylimidazo[1,2-a]pyridine-3-acetamide•hydrochloride | |
| 27 | N-ethyl-N-(4-pyridinylmethyl)-2-(4-methylphenyl)-6-methylimidazo[1,2-a]pyridine-3-acetamide•hydrochloride | |
| 28 | N-ethyl-N-(4-pyridinylmethyl)-2-(4-chlorophenyl)-6-methylimidazo[1,2-a]pyridine-3-acetamide•hydrochloride | |

In one embodiment of the present invention, the compound is N-ethyl-N-(2-pyridinylmethyl)-2-(3,4-dichlorophenyl)-7-methylimidazo[1,2-a]pyridine-3-acetamide.hydrochloride and N-ethyl-N-(4-pyridinylmethyl)-2-(3,4-dichlorophenyl)-7-methylimidazo[1,2-a]pyridine-3-acetamide.hydrochloride.

Another aspect of the present invention relates to a method for preparing the above compound of Formula I, its tautomer, its racemic or optical isomer, its pharmaceutically acceptable salt, or its solvate, comprising the following steps:

a) converting an aromatic hydrocarbon compound of Formula VIII:

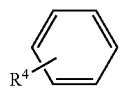

VIII via Friedel-Crafts acetylation to form a ketone compound of Formula VII:

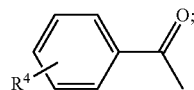

VII b) reacting the ketone compound VII with bromine under the catalysis of aluminum trichloride to form a bromide, not being separated, reacting with an aminopyridine compound of Formula VI,

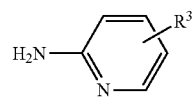

VI under heating and presence of an alkali (such as sodium carbonate) to form an imidazopyridine compound of Formula V:

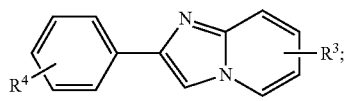

V c) reacting the imidazopyridine compound V with dimethylamine and formaldehyde aqueous solution in acetic acid to form a Mannich base, separating via filtration, then reacting with iodomethane to form a quaternary ammonium salt of Formula IV:

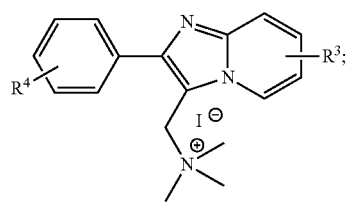

IV d) reacting the quaternary ammonium salt IV with a cyanide (such as sodium cyanide or potassium cyanide) to form a corresponding nitrile, then hydrolyzing in the presence of a strong base, and acidifying to form a carboxylic compound of Formula II:

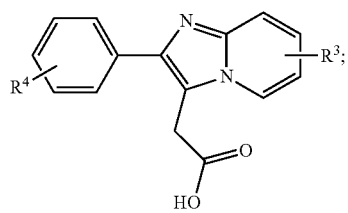

II e) in the presence or absence of a catalyst, such as 4-dimethylaminopyridine, reacting the carboxylic compound of Formula II as obtained in step d) with an amine compound of Formula III in the presence of a condensing agent (such as 1-ethyl-3-(3-diisopropylaminopropyl)carbodiimide (EDC) or 1,3-dicyclohexylcarbodiimide (DCC)):

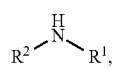

III to obtain a compound of Formula I:

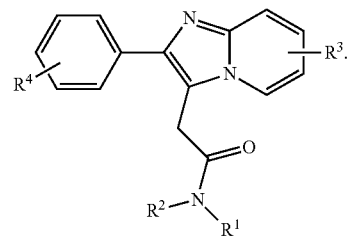

I

According to the teachings of the present invention, the compound of Formula I of the present invention can be synthesized on the basis of the knowledge in the art.

In one embodiment of the method for preparing the compound of Formula I of the present invention, a corresponding substituted aromatic hydrocarbon is subjected to Friedel-Crafts acetylation, bromination, then condensation with 2-aminopyridine to form a corresponding 2-arylimidazo[1,2-a]pyridine V, the latter is then subjected to Mannich reaction and methylation to form a corresponding quaternary ammonium salt IV of 3-methylaminomethyl, then reacts with a cyanide, then is subjected to hydrolysis and acidification to form a corresponding 2-arylimidazo[1,2-a]pyridine-3-acetic acid precursor II, and finally subjected to condensation with a substituted secondary amine in the presence of 1-ethyl-3-(3-dimethylaminopropyl)carbodiimide (EDC) to obtain an amide compound of Formula I. The reaction scheme is as follows:

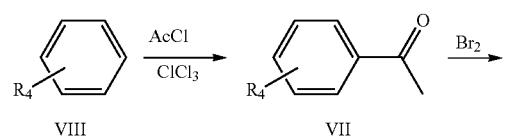

-continued

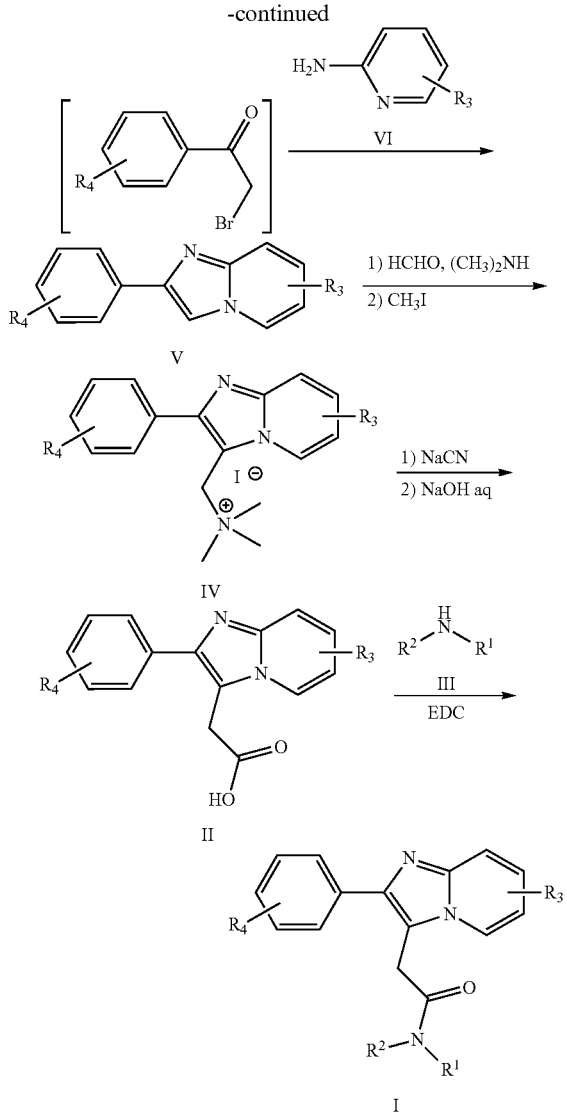

The substituted secondary amine is prepared from a corresponding primary amine and a substituted aldehyde via reductive alkylation or catalytic hydrogenation; or prepared by converting a substituted alcohol into its halogenide or active ester, then reacting with a corresponding primary amine. The reaction schemes are as follows:

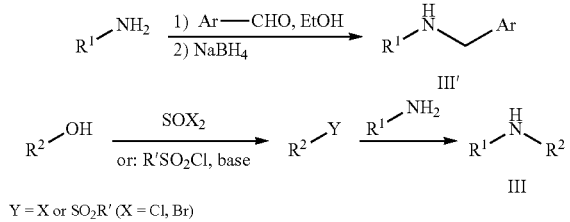

Y = X or $SO_2R'$ (X = Cl, Br)

Optionally, the method for preparing the above compound of Formula I, its tautomer, its racemic or optical isomer, its pharmaceutically acceptable salt, or its solvate, comprises the following steps:

a) converting an aromatic hydrocarbon compound of Formula VIII:

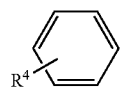

VIII via Friedel-Crafts acetylation using succinic anhydride to form a ketonic acid compound of Formula VII':

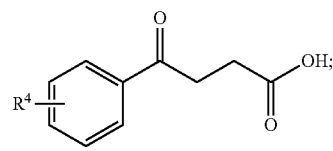

VIII' b) subjecting the above ketonic acid compound of Formula VIII' to bromination with bromine to form a brominated acid compound of Formula VII':

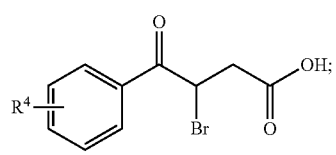

VII' c) reacting the above brominated acid compound of Formula VII' with a chloroformate (such as ethyl chloroformate or isobutyl chloroformate) to form a mixed acid anhydride, then reacting with an amine of Formula III

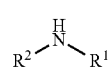

III in the presence or absence of a catalyst (such as DMAP), and in the presence of an alkali to form a bromonated amide compound of Formula II':

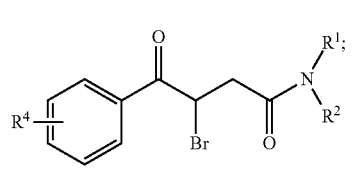

II' d) subjecting the above bromonated amide compound of Formula II' and an aminopyridine compound of Formula VI:

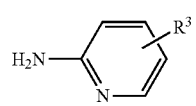

VI to condensation in the presence of an alkali to prepare a compound of Formula I:

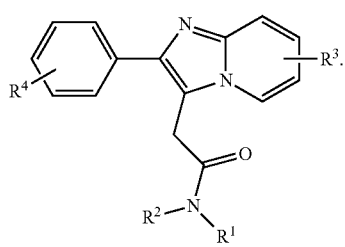

According to the preparation method of the present invention, the amine compound of Formula III is prepared from a primary amine $R^1$—$NH_2$ and a corresponding aldehyde via reductive amination or catalytic hydrogenation amination; or prepared by reacting a corresponding alcohol $R^2$—OH with halogenated sulfoxide to form a corresponding halogenide $R^2$—X, or with sulfonyl chloride to form an active ester $R^2$—$OSO_2R$, then reacting with a primary amine $R^1$—$NH_2$ in the presence or absence of an alkali to prepare the amine III.

In another embodiment of the method for preparing the compound of Formula I of the present invention, a substituted aromatic hydrocarbon VIII is subjected to Friedel-Crafts acetylation using succinic anhydride to form 4-aryl-4-oxybutanoic acid VIII', then bromination to form a bromide VII', then conversion to form an ester VI', then condensation with a corresponding 2-aminopyridine V to form 2-arylimidazo[1,2-a]pyridine IV', the hydrolysis to form a corresponding acid II, and finally reaction with an amine III in the presence of condensing agent EDC to form the target compound amide I. The reaction scheme is as follows:

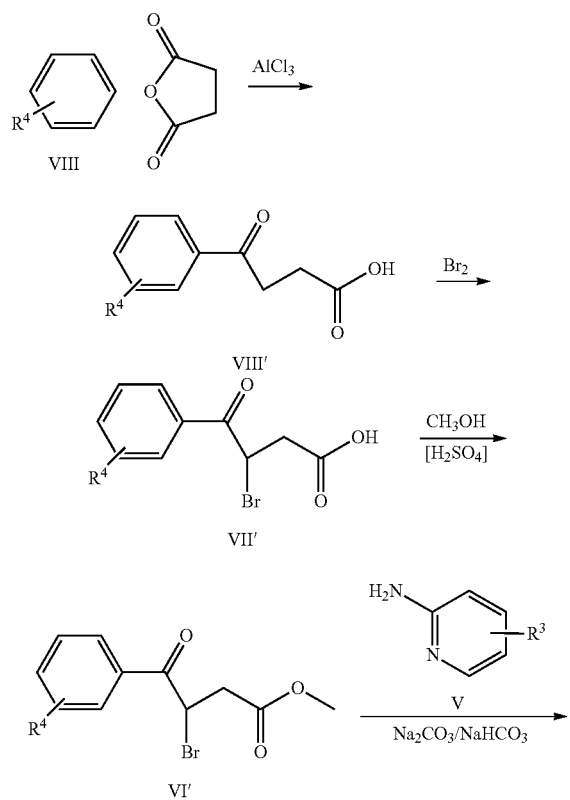

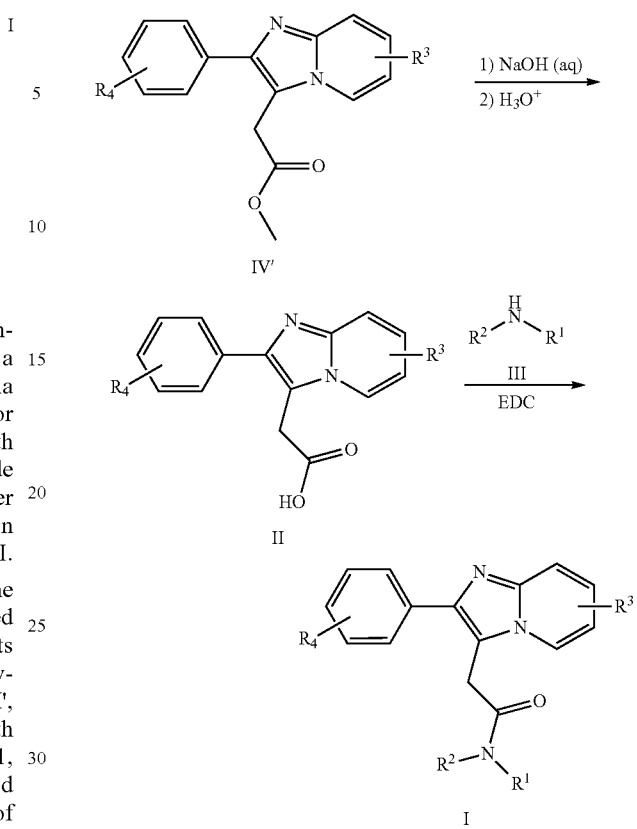

In another embodiment of the method for preparing the compound of Formula I of the present invention, a substituted aromatic hydrocarbon VIII is subjected to Friedel-Crafts acetylation using succinic anhydride to form 4-aryl-4-oxybutanoic acid VIII', then bromination to form a bromide VII', then conversion by mixed anhydride method to form an amide II', then condensation with a corresponding 2-aminopyridine V to form the target compound 2-arylimidazo[1,2-a]pyridine-3-acetamide I. The reaction scheme is as follows:

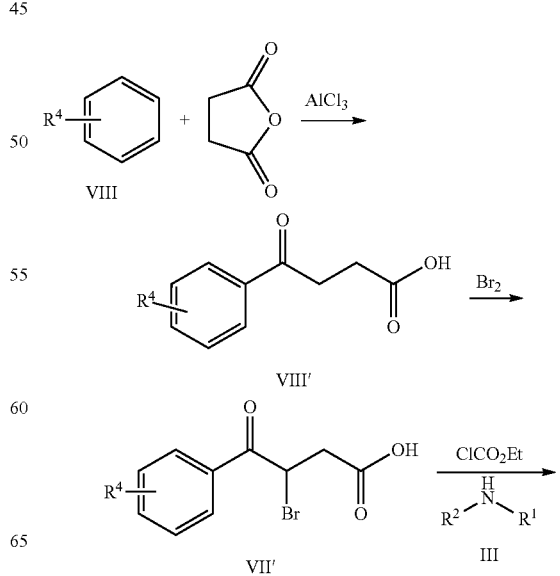

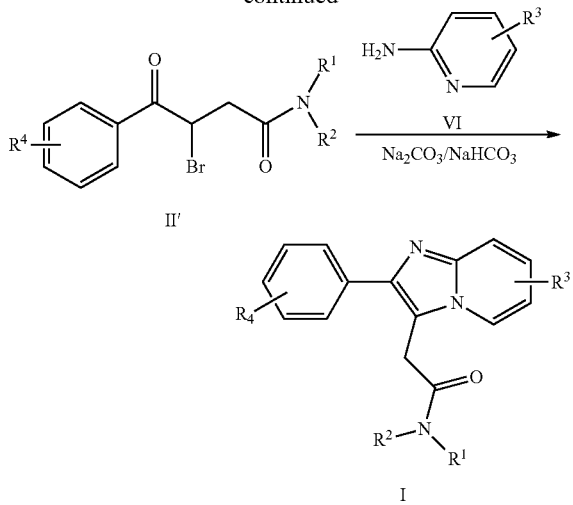

In the method for synthesis of the compound of Formula I according to the present invention, the raw materials used in the reactions are all obtainable by those skilled in the art according to the existing knowledge, or can be prepared by known methods in the documents in the art, or commercially available. The intermediates, raw materials, reagents and reaction conditions used in the above reaction schemes can be suitably changed by those skilled according to the knowledge in the art. Otherwise, those skilled in the art can prepare other compounds of Formula I that are not specifically listed in the text according to the preparation method of the second aspect of the present invention.

The further another aspect of the present invention relates to a pharmaceutical compound, which comprises at least one the above compound of Formula I, its tautomer, its racemic or optical isomer, its pharmaceutically acceptable salt, or its solvate, and optionally a pharmaceutically acceptable carrier or excipient.

The pharmaceutical composition can be applied to animals, preferably mammals, especially human. Generally, the pharmaceutical composition of the present invention comprises 0.1-90 wt. % of the compound of Formula I and/or its physiologically acceptable salt. The pharmaceutical composition can be prepared according to known methods in the art. For this purpose, if necessary, the compound of Formula I and/or stereoisomer thereof is combined with one or more solid or liquid pharmaceutically acceptable excipient and/or adjuvant, to prepare a suitable administration form or dosage form for human use.

The compound of Formula I or the pharmaceutical composition comprising the same according to the present invention can be administered in unit dosage form, via administration route such as intestinal route or parenteral route, such as oral, muscle, subcutaneous, nasal cavity, mouth mucosa, skin, peritoneum or rectum. The administration dosage form can be for example tablets, capsules, dropping pills, aerosols, pills, powders, solutions, suspensions, emulsions, granules, liposomes, transdermal agents, buccal tablets, suppositories, lyophilized powders, etc., can be normal preparations, sustained release preparations, controlled release preparations, and various particle drug delivery systems. In order to manufacture tablets of unit dosage form, various carriers known in the art can be widely used. The examples of carriers can be diluents and absorbents, such as starches, dextrin, calcium sulfate, lactose, mannitol, sucrose, sodium chloride, glucose, urea, calcium carbonate, porcellanite, microcrystalline cellulose, aluminum silicate; wetting agents and binding agents, such as water, glycerol, polyethylene glycol, ethanol, propanol, starch slurry, dextrin, syrup, honey, glucose solution, Arabic gum gel, gelatin gel, carboxylmethylcellulose sodium, shellac, methylcellulose, potassium phosphate, polyvinylpyrrolidone; disintegrants, such as dry starch powder, alginate, agar powders, laminarin, sodium hydrogen carbonate and citric acid, calcium carbonate, polyoxyethylene sorbitol fatty acid ester, sodium dodecylsulfonate, methylcellulose, ethylcellulose; disintegration inhibitors, such as sucrose, glycerol tristearate, cocoa butter, hydrogenated oil; absorption enhancers, such as quaternary ammonium salts, sodium dodecylsulfate; lubricants, such as talc powder, silica, corn starch, stearate, boric acid, liquid paraffin, polyethylene glycol. The tablets can be further processed to form coating tablets, such as sugar coated tablets, thin film coated tablets, enteric coating tablets, or bilayer tablets and multilayer tablets. In order to manufacture pills of administration unit, various carriers known in the art can be widely used. The examples of these carriers include, for example, diluents and absorbents, such as glucose, lactose, starches, cocoa butter, hydrogenated vegetable oil, polyvinylpyrrolidone, Gelucire, kaolin, talc powder, etc.; binding agents such as Arabic gum, tragacanth gum, gelatin, ethanol, honey, liquid sugar, rice paste or panada; disintegrants, such as agar powders, dry starch powder, alginate, sodium dodecylsulfonate, methylcellulose, ethylcellulose. In order to manufacture suppositories of the administration unit, various carriers known in the art can be widely used. The examples of these carriers include, for example, polyethylene glycol, lecithin, cocoa butter, higher alcohol, esters of higher alcohols, gelatin, semi-synthesized glycerides. In order to manufacture capsules of the administration unit, the compound of Formula I or its stereoisomer as effective component is mixed with the above various carriers, and the resultant mixture is placed in hard gelatin capsules or soft capsules. The compound of Formula I or its stereoisomer as effective component can also be processed to form microcapsules, which can be suspended in an aqueous medium to form a suspension, or filled in hard capsules or converted into injections. In order to manufacture of injection preparations of the administration unit, such as solutions, emulsions, lyophilized powder for injection and suspensions, various carriers known in the art can be widely used, for example, water, ethanol, polyethylene glycol, 1,3-propanediol, ethoxylated isostearyl alcohol, multi-oxidized isostearyl alcohol, polyoxyethylene sorbitol fatty acid esters. In addition, in order to manufacture isosmotic injection solutions, a suitable amount of sodium chloride, glucose or glycerol can be added to injection preparations. Further, conventional co-solvents, buffer agents, pH regulators can also be added.

In addition, if desired, coloring agents, preservatives, perfumes, correctant, sweeting agents or other materials can also be added.

The term "composition" in the text refers to a product comprising various components in designated amounts, and any product directly or indirectly derived from various components in designated amounts in combination.

The further aspect of the present invention relates to a use of the compound of Formula I, its tautomer, its racemic or optical isomer, its pharmaceutically acceptable salt, or its solvate, as TSPO ligand.

The further aspect of the present invention relates to a use of the compound of Formula I, its tautomer, its racemic or optical isomer, its pharmaceutically acceptable salt, or its solvate, in manufacture of a medicament or reagent for regulating TSPO activity.

The further aspect of the present invention relates to a use of the compound of Formula I, its tautomer, its racemic or optical isomer, its pharmaceutically acceptable salt, or its solvate in manufacture of a medicament for prophylaxis or treatment of a central nervous system disease associated with TSPO dysfunction. Specifically, the central nervous system disease associated with TSPO dysfunction is depression, anxiety, mania, cognitive defect, schizophrenia, pains, convulsion, drug dependence, sleep disorders, ingestion disorders, alcoholism, nerve injury, or stress disorders.

The further aspect of the present invention relates to a use of the compound of Formula I, its tautomer, its racemic or optical isomer, its pharmaceutically acceptable salt, or its solvate, in manufacture of a medicament for combating cell apoptosis, anti-tumors, inflammatory immunoregulation, or neuroprotection.

The further aspect of the present invention relates to a method for prophylaxis and/or treatment of a central nervous system disease associated with TSPO dysfunction, such as depression, anxiety, cognitive defect, convulsion, drug dependence, pains, sleep disorders, ingestion disorders, alcoholism, as well as for anti-cell apoptosis, anti-tumors, inflammatory immunoregulation, neuroprotection, or regulating TSPO activity in vivo or in vitro, the method comprises a step of administering a subject in such need a prophylactically and/or therapeutically effective amount of the compound of Formula I, its tautomer, its raceme or stereoisomer, its pharmaceutically acceptable salt, or its solvate. The medicament is useful in animals, preferably mammals, especially human.

The dose of the compound of Formula I of the present invention, its tautomer, its racemic or optical isomer, its pharmaceutically acceptable salt, or its solvate, depends on many factors, such as property and severity of the disease to be prevented or treated, patient's or animal's gender, age, body weight and individual reaction, the specific compound to be used, administration route, and administration frequency. The dose can be administered in single dose form or in several batches, such as 2-, 3- or 4-batches.

The actual dose levels of various active components in the pharmaceutical composition of the present invention can be changed so that the expected therapeutic effects can be achieved via the resultant amount relative to specific patient, composition and administration manner. The dose level must be selected according to the activity of the specific compound, administration route, severity of disease to be treated, patient's condition and medical history. However, the practice in the art is that the dose of compound gradually increases from a level lower than that for achieving the desired therapeutical effects to a dose capable of achieving the desired therapeutical effects.

In the aforementioned or other treatment and/or prophylaxis, a compound of the present invention in a therapeutically and/or prophylactically effective amount can be used in form of pure compound, or in form of pharmaceutically acceptable esters or prodrugs thereof (if they exist). Alternatively, the compound can be administered via a pharmaceutical composition comprising the compound and one or more pharmaceutically acceptable excipients. The term a compound of the present invention in a "therapeutically and/or prophylactically effective amount" means that the compound is in an amount sufficient to achieve prophylactically and/or therapeutically reasonable ratio of effect/risk. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the used specific compound, the used specific composition, the age, body weight, general health status, gender and food of patient, the administration time and route and excretory rate of the used specific compound, the drug(s) administered in combination or simultaneously with the specific compound, and similar factors well known in the art of medicine. For example, it is a common method in the art to increase gradually the dose of compound from a level lower than that for achieving desired therapeutical effects to a level enough to achieve the desired therapeutical effects. In general, the dose of a compound of Formula I for mammals especially human can be 0.001-1000 mg/kg body weight per day, such as 0.01-100 mg/kg body weight per day, 0.01-10 mg/kg body weight per day.

The compound of Formula I, its tautomer, its racemic or optical isomer, its pharmaceutically acceptable salt, or its solvate, according to the present invention, can effectively prevent and/or treat the various diseases and disorders as mentioned in the present invention.

The inventors find via researches that the compound of Formula I has function of regulating TSPO, so that this type of compounds can be used in a central nervous system disease associated with TSPO dysfunction, such as depression, anxiety, cognitive defect, convulsion, drug dependence, pains, sleep disorders, ingestion disorders, alcoholism, as well as for anti-cell apoptosis, anti-tumors, inflammatory immunoregulation, neuroprotection. Further synthesis and researches indicate that a pharmaceutically acceptable salt of a derivative of the present invention form with a suitable inorganic acid or organic acid or with an inorganic alkali or organic alkali would also have effect in regulating TSPO function.

All documents as cited in the present invention are incorporated in the text by reference, and if the meanings of these documents are inconsistent with the present invention, the expressions of the present invention should be used. In addition, the terms and phrases used in the present invention has common meanings well known by those skilled in the art, nevertheless, these terms and phrases are further explained and illustrated in the invention. If the mentioned terms and phrases have meanings different from those known in the art, the meanings present in the present invention should be used.

The terms "halo", "halogen", "Hal" or "halogenated" refer to fluorine, chlorine, bromine and iodine.

In the present invention, the used terms "alkyl", "alkenyl" and "alkynyl" have the common meanings well known in the art, that is, they are straight or branched hydrocarbon groups, for example but not limited to methyl, ethyl, propyl, isopropyl, n-butyl, sec-butyl, tert-butyl, allyl, propenyl, propinyl, etc., and the "alkyl", "alkenyl" and "alkynyl" can be collectively called as "hydrocarbonyl" or "aliphatic hydrocarbonyl". In a preferable embodiment of the present invention, the term "hydrocarbonyl" refers to alkane, including alkyl and cyclic alkyl, especially alkyl such as $C_1$-$C_6$ alkyl.

In the present invention, the term "substituted or unsubstituted $C_1$-$C_6$ alkyl" refers to a substituted or unsubstituted alkyl group having designated carbon atoms, its examples include but are not limited to: methyl, ethyl, propyl, isopropyl, butyl, tert-butyl, pentyl, neopentyl, hexyl.

In the present invention, the term "central nervous system disease associated with TSPO dysfunction" refers to a central nervous system disease directly or indirectly induced by TSPO dysfunction, such as depression, anxiety, mania, cognitive defect, schizophrenia, pains, convulsion, drug dependence, sleep disorders, ingestion disorders, alcoholism, nerve injury, stress disorders, etc.

SPECIFIC MODELS FOR CARRYING OUT THE INVENTION

Figure 1:
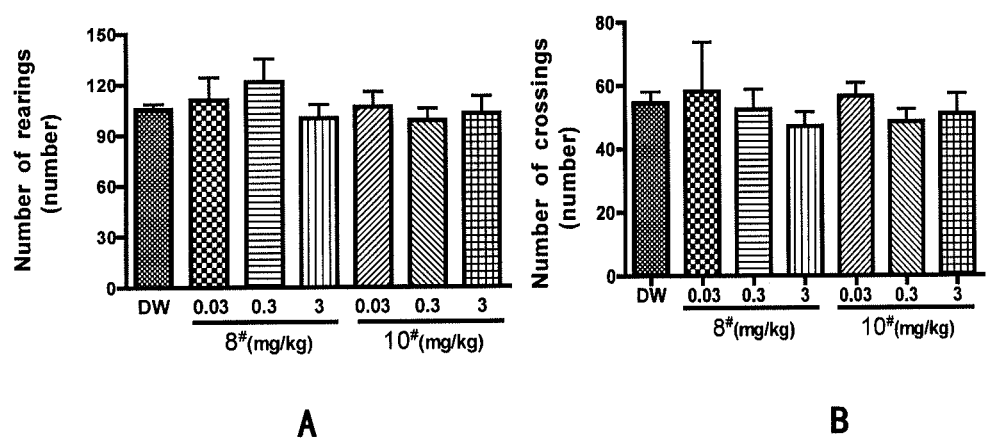
FIG. 1: Effects of Example Compounds 8 and 10 on open field spontaneous locomotor activity in mice. The results are shown in $\bar{x}\pm s$, n=9-10. *$P<0.05$ in comparison with DW group.

The present invention is further illustrated with the following examples, but those skilled in the art would understand the following examples are merely used to illustrate the present invention, rather than to limit the protection scope of the present invention. For those technologies or conditions not specifically described in the examples, they were performed according to the technologies or conditions as described in the documents in the art or according to the product specifications. For those reagents and instruments whose manufacturers were not given, they were all conventional products commercially available in markets.

The synthesis of important intermediates involved in the present invention is illustrated in Examples 1-12.

Example 1

Synthesis of 2-arylimidazo[1,2-a]-pyridine-3-acetic acid ($V_1$)

a) 2-(4-methoxyphenyl)-7-methylimidazo[1,2-a]pyridine ($II_1$): 15.02 g (0.1 mol) of 4-methoxyphenylethylketone was dissolved in 50 mL of methanol, added with 0.7 g (0.005 mol) of anhydrous aluminum trichloride, stirred in ice-water bath, added dropwise with 16.16 g (5.2 mL, 0.101 mol) of liquid bromine, (color immediately faded, white solid was precipitated near to the end of dropwise addition), after the end of addition, further stirred for 20 min, added with 25 mL of water, then added with 13.5 g (0.127 mol) of solid sodium carbonate, then added with 11.5 g (0.106 mol) of solid 2-amino-4-methylpyridine, heated to 35° C., stirred overnight (14 h), and terminated reaction. Added with 100 mL of water, stirred in ice-water bath (white solid precipitated), suction filtrated, washed with water, dried to obtain $II_1$ 20.28 g, yellow solid powder, yield 85%. m.p. 157-160° C.

b) 1-(2-(4-methoxyphenyl)-7-methylimidazo[1,2-a]-3-pyridinyl)-N,N-dimethylamine ($III_1$): 20.28 g (0.085 mol) of $II_1$ was weighed, dissolved in 30 ml of acetic acid, stirred under room temperature, added dropwise with 14.5 g (0.106 mol) of dimethylamine aqueous solution (33%), (with slight heat release, solid appeared and dissolved immediately), then added dropwise with 8.5 g (0.105 mol) of formaldehyde aqueous solution (37%), after the end of addition, heated to 35° C. and stirred for 2 h, stopped reaction. In ice-water bath, regulated with sodium hydroxide aqueous solution to reach pH 8-9, extracted with dichloromethane, washed with water, saturated saline in order, dried with anhydrous sodium sulfate overnight, evaporated to remove solvent to obtain thick liquid $III_1$ (crude product) 25.78 g.

c) 2-(4-methoxyphenyl)-7-methylimidazo[1,2-a]-pyridine-3-acetic acid ($V_1$): 25.78 g (0.087 mol) of $III_1$ was dissolved in 150 ml of acetone, stirred at room temperature, added dropwise with 5.5 ml (0.088 mol) of iodomethane, solid precipitated before the end of addition, after the end of addition, reacted overnight (20 h), stopped the reaction. Filtered and washed with acetone, dried to obtain 27.8 g of quaternary ammonium salt $IV_1$, crude yield 75%. $^1$H NMR (DMSO-$d_6$, 400 MHz)δ:2.42(s, 3H), 2.86(s, 9H), 3.82(s, 3H), 5.2(s, 2H), 7.00(d, 1H, J=7.00 Hz), 7.04-7.06(m, 2H), 7.50(s, 1H), 7.77-7.79(m, 2H), 8.82(d, 1H, J=7.00 Hz).

27.8 g (0.064 mol) of the above prepared quaternary ammonium salt ($IV_1$) crude product was dissolved in 120 mL of a mixture solution of water and dioxane ($V_{water}$:$V_{dioxane}$=2:1), then added with 20 mL of polyethylene-400, added with 3.1 g (0.064 mol) of sodium cyanide, heated to 85° C. and reacted for 4 h, monitored with TLC until the completion of reaction. Cooled to room temperature, added with 29 g (0.725 mol) of sodium hydroxide solid, heated to 110° C. and refluxed for 24 h, monitored until no more ammonia gas generated, stopped the reaction. Cooled, extracted with dichloromethane; stirred under ice-bath, the water phase was acidified with concentrated hydrochloric acid then acidified with acetic acid to reach pH=5-6, a solid was precipitated, suction filtered, dried to obtain 2-(4-methoxyphenyl)-7-methylimidazo[1,2-a]-pyridine-3-acetic acid ($V_1$) as yellowish solid powder, 9.03 g, yield 51%. m.p. 234-236° C. (decomposition), $^1$H NMR(DMSO-$d_6$, 400 MHz)δ: 2.47(s, 3H), 3.83 (s, 3H), 4.14(s, 2H), 7.10(d, 1H, J=7.00 Hz), 7.12-7.14(m, 2H), 7.54(s, 1H), 7.65-7.67(m, 2H), 8.53(d, 1H, J=7.00 Hz), 13.14(s, 1H).

Examples 2-6

Synthesis of Compounds $V_2$-$V_6$

In Examples 2-6, by referring to the method of Example 1 for synthesizing Compound $V_1$, the following Compounds $V_2$-$V_6$ were synthesized.

2-(4-chlorophenyl)-7-methylimidazo[1,2-a]-pyridine-3-acetic acid ($V_2$): light yellow solid powder, yield 20%. m.p. 229-231° C., $^1$H NMR(DMSO-$d_6$, 400 MHz)δ: 2.42(s, 3H), 4.17(s, 2H), 7.06(d, 1H, J=7.00 Hz), 7.53(s, 1H), 7.57-7.62 (m, 2H), 7.76-7.78(m, 2H), 8.48(d, 1H, J=7.00 Hz), 12.96(s, 1H).

2-(4-methylphenyl)-7-methylimidazo[1,2-a]pyridine-3-acetic acid ($V_3$): white solid powder, yield 61.6%. m.p. 220-224° C. (decomposition), $^1$H NMR(DMSO-$d_6$, 400 MHz) δ: 2.35(s, 3H), 2.38(s, 3H), 4.08(s, 2H), 6.80(d, 1H, J=7.00 Hz), 7.27-7.29(m, 2H), 7.36(s, 1H), 7.63-7.65(m, 2H), 8.26(d, 1H, J=7.00 Hz).

2-(3,4-dichlorophenylethylketone)-7-methylimidazo[1,2-a]pyridine -3-acetic acid ($V_4$): light yellow solid powder, yield 63.8%. m.p. 238-240° C., ESI-MS m/z: 335[M+H$^+$], $^1$H NMR(DMSO-$d_6$, 400 MHz)δ: 2.38(s, 3H), 4.15(s, 2H), 6.85 (d, 1H, J=7.00 Hz), 7.39(s, 1H), 7.75(s, 2H), 7.98(s, 1H), 8.31(d, 1H, J=7.00 Hz), 12.85(s, 1H).

2-(4-methylphenyl)-6-methylimidazo[1,2-a]pyridine-3-acetic acid ($V_5$): white solid powder, yield 85.3%. m.p. 237-239° C. (decomposition), ESI-MS m/z: 281[M+H]$^+$, $^1$HNMR (DMSO-$d_6$, 400 MHz)δ: 2.33(s, 3H), 2.35(s, 3H), 4.09(s, 2H), 7.14(d, 1H, J=9.24 Hz), 7.27-7.29 (m, 2H), 7.50(d, 1H, J=9.24 Hz), 7.62-7.64(m, 2H), 8.21 (s, 1H), 12.74(s, 1H).

2-(4-chlorophenyl)-6-methylimidazo[1,2-a]pyridine-3-acetic acid ($V_6$): light yellow solid powder, yield 18.5%. $^1$H NMR (DMSO-$d_6$, 400 MHz)δ: 2.33(s, 3H), 4.12(s, 2H), 7.17-7.19(m, 1H), 7.52-7.53(m, 1H), 7.54-7.56(m, 2H), 7.75-7.78 (m, 2H), 8.24(s, 1H), 12.86(s, 1H).

Example 7

Synthesis of N-(arylmethyl)ethylamine

N-(4-pyridinylmethyl)ethylamine ($VI_1$): 15.70 g (0.147 mol) of 4-pyridine-formaldehyde was dissolved in 200 mL of ethanol, added under stirring in cold-water-bath with 21 g (0.296 mol) of 65-70% ethylamine aqueous solution, reacted for 0.5 h, monitored with TLC until the reaction was almost completed. Added carefully with 5.6 g (0.148 mol) of sodium borohydride in several batches, small amount in each batch, after the end of addition, added with 30 mL of water, reacted overnight (20 h), the reaction was completed according to TLC monitoring. Evaporated to remove solvent, added with water, extracted with dichloromethane, washed with water and saturated saline in order, dried with anhydrous sodium sulfate, evaporated to remove solvent to obtain yellow thick liquid, 30 g, crude yield 73.4%. $^1$H NMR(CDCl$_3$, 400 MHz) δ: 1.14(t, 3H, J=7.00 Hz), 2.66(q, 2H, J=7.00 Hz), 3.81(s, 2H), 7.26-7.27(m, 2H), 8.52-8.54(m, 2H).

Examples 8-12

Synthesis of Compounds $VI_2$-$VI_6$

In Examples 8-12, referring to the method of Example 7 for synthesizing Compound $VI_1$, the following Compounds $VI_2$-$VI_6$ were synthesized, respectively.

N-benzylethylamine ($VI_2$): 12.4 g, crude yield 92%;
N-(3-pyridinylmethyl)ethylamine ($VI_3$): 47 g, crude yield 96%;
N-(2-pyridinylmethyl)ethylamine ($VI_4$): 19 g, crude yield 46.6%;
N-(2-pyridinylmethyl)-2-methoxyethylamine ($VI_5$): 13.17 g, crude yield 79.3%;
N-(3-pyridinylmethyl)-2-methoxyethylamine ($VI_6$): 16 g, crude yield 97%.

TLC showed that the above products contained a small amount of tertiary amine as by-product, but which did not influence the following condensation to form amide, so that they could be directly used in the next synthesis.

The following Examples 13-40 were examples for synthesis of Compounds 1-28 of the present invention.

Example 13

Synthesis of N-benzyl-N-ethyl-2-(4-chlorophenyl)-7-methylimidazo[1,2-a]pyridine-3-acetamide (Compound 1)

0.9 g (0.003 mol) of 2-(4-chlorophenyl)-7-methylimidazo [1,2-a]-pyridine-3-acetic acid and 0.6 g (0.0045 mol) of N-benzylethylamine were weighed, added to 80 mL of dry dichloromethane, then added with 1.0 g (0.005 mol) of EDC hydrochloride. Stirred at room temperature and reacted for 24 h, stopped the reaction until almost completion of the reaction. Filtered to remove solid urea, concentrated, and then separated with silica gel column chromatograph to obtain a crude product which was recrystallized with acetone to obtain a pure white solid powder, 0.5 g in total, yield 39.9%. m.p. 192-193° C., ESI-MS m/z: 419[M+H]$^+$, $^1$H NMR (CDCl$_3$, 400 MHz)δ: 1.20(t, 3H, J=7.00 Hz), 2.54(s, 1.7H), 2.56(s, 1.3H), 3.38(q, 0.8H, J=7.00 Hz), 3.57(q, 1.2H, J=7.00 Hz), 4.11(s, 1H), 4.21(s, 1H), 4.59(s, 0.7H), 4.62(s, 1.3H), 7.09-7.15(m, 2H), 7.24-7.37(m, 5H), 7.46-7.56(m, 2H), 7.69-7.71 (m, 1H), 8.09-8.23(m, 2H).

Example 14

N-ethyl-N-(2-pyridinylmethyl)-2-(4-chlorophenyl)-7-methylimidazo[1,2-a]pyridine-3-acetamide.hydrochloride (Compound 2)

According to the method of Example 13, 2-(4-chlorophenyl)-7-methylimidazo[1,2-a]pyridine-3-acetic acid and N-(2-pyridinylmethyl)ethylamine were used as raw materials for synthesis, salified with hydrochloric acid-ethyl ether solution in dry dichloromethane, then crystallized with methanol-tetrahydrofuran to obtain a corresopnding hydrochloride pure product. Yellow solid powder, yield 51.2%. m.p. 178-180° C., ESI-MS m/z: 420[M+H]$^+$, $^1$H NMR(D$_2$O, 400 MHz)δ: 0.95 (t, 0.5H, J=7.00 Hz), 1.14(t, 2.5H, J=7.00 Hz), 2.38(s, 2.5H), 2.40(s, 0.5H), 3.30(q, 0.4H, J=7.00 Hz), 3.56(q, 1.6H, J=7.00 Hz), 4.14(s, 0.4H), 4.36(s, 1.6H), 4.76(s, 1.6H), 4.86(s, 0.4H), 7.14-7.24(m, 1H), 7.30-7.46(m, 4H), 7.50(s, 1H), 7.69-7.75(m, 2H), 8.11-8.13(m, 1H), 8.33-8.53(m, 2H).

Example 15

N-ethyl-N-(3-pyridinylmethyl)-2-(4-chlorophenyl)-7-methylimidazo[1,2-a]pyridine-3-acetamide.hydrochloride (Compound 3)

According to the method of Example 14, 2-(4-chlorophenyl)-7-methylimidazo[1,2-a]pyridine-3-acetic acid and N-(3-pyridinylmethyl)ethylamine were used as raw materials for synthesis, to obtain light yellow solid powder, yield 69.5%. m.p. 236-238° C., ESI-MS m/z: 420[M+H]$^+$, $^1$H NMR(D$_2$O, 400 MHz)δ: 0.95(t, 0.7H, J=7.00 Hz), 1.11(t, 2.3H, J=7.00 Hz), 2.39(s, 2.3H), 2.40(s, 0.7H), 3.27(q, 0.5H, J=7.00 Hz), 3.48(q, 1.5H, J=7.00 Hz), 4.13(s, 0.5H), 4.32(s, 1.5H), 4.60(s, 1.5H), 4.71(s, 0.5H), 7.15-7.22(m, 1H), 7.32-7.44(m, 4H), 7.51(s, 1H), 7.84(m, 1H), 8.12-8.14(m, 1H), 8.26(m, 1H), 8.52-8.53(m, 2H).

Example 16

N-ethyl-N-(4-pyridinylmethyl)-2-(4-chlorophenyl)-7-methylimidazo[1,2-a]pyridine-3-acetamide.hydrochloride (Compound 4)

According to the method of Example 14, 2-(4-chlorophenyl)-7-methylimidazo[1,2-a]pyridine-3-acetic acid and N-(4-pyridinylmethyl)ethylamine were used as raw materials for synthesis, yellow solid powder, yield 69.5%. m.p. 245-247° C., ESI-MS m/z: 420[M+H]$^+$, $^1$H NMR(D$_2$O, 400 MHz)δ: 0.95(t, 0.7H, J=7.00 Hz), 1.11(t, 2.3H, J=7.00 Hz), 2.38(s, 2.3H), 2.39(s, 0.7H), 3.27(q, 0.5H, J=7.00 Hz), 3.52 (q, 1.5H, J=7.00 Hz), 4.06(s, 0.5H), 4.39(s, 1.5H), 4.66(s, 1.5H), 4.88(s, 0.5H), 7.16-7.28(m, 2H), 7.35-7.47(m, 4H), 7.50(s, 1H), 7.65-7.66(m, 1H), 8.14-8.26(m, 1H), 8.44-8.51 (m, 2H).

Example 17

N-(2-methoxyethyl)-N-(2-pyridinylmethyl)-2-(4-chlorophenyl)-7-methylimidazo[1,2-a]pyridine-3-acetamide.hydrochloride (Compound 5)

According to the method of Example 14, 2-(4-chlorophenyl)-7-methylimidazo[1,2-a]pyridine-3-acetic acid and N-(2-pyridinylmethyl)-2-methoxyethylamine were used as raw materials for synthesis, white solid powder, yield 46.0%. m.p. 238-239° C., ESI-MS m/z: 450[M+H]$^+$, $^1$H NMR(D$_2$O, 400 MHz)δ: 2.37(s, 2.5H), 2.39(s, 0.5H), 3.10(s, 0.5H), 3.14 (s, 2.5H), 3.52(t, 2H, J=4.76 Hz) 3.74(t, 2H, J=4.76 Hz), 4.15(s, 0.4H), 4.41(s, 1.6H), 4.76(s, 1.6H), 4.85(s, 0.4H), 7.15-7.23(m, 1H), 7.30-7.47(m, 4H), 7.50(s, 1H), 7.60-7.70 (m, 2H), 8.09-8.11(m, 1H), 8.25-8.45(m, 2H).

Example 18

N-(2-methoxyethyl)-N-(3-pyridinylmethyl)-2-(4-chlorophenyl)-7-methylimidazo[1,2-a]pyridine-3-acetamide.hydrochloride (Compound 6)

According to the method of Example 14, 2-(4-chlorophenyl)-7-methylimidazo[1,2-a]pyridine-3-acetic acid and N-(3-pyridinylmethyl)-2-methoxyethylamine were used as raw materials for synthesis, white solid powder, yield 69.4%. m.p. 234-235° C., ESI-MS m/z: 450[M+H]$^+$, $^1$H NMR (DMSO-d$_6$, 400 MHz) δ: 2.39(s, 2.4H), 2.40(s, 0.6H), 3.10(s, 0.6H), 3.11(s, 2.4H), 3.48(t, 2H, J=4.76 Hz), 3.68(t, 2H, J=4.76 Hz), 4.14(s, 0.4H), 4.38(s, 1.6H), 4.63(s, 1.6H), 4.83 (s, 0.4H), 7.16-7.22(m, 1H), 7.34-7.47(m, 4H), 7.51(s, 1H), 7.80-7.82(m, 1H), 8.10-8.12(m, 1H), 8.21-8.27(m, 1H), 8.48-8.51(m, 2H).

Example 19

N-benzyl-N-ethyl-2-(3,4-dichlorophenyl)-7-methylimidazo[1,2-a]pyridine-3-acetamide (Compound 7)

According to the method of Example 13, 2-(3,4-dichlorophenyl)-7-methylimidazo[1,2-a]pyridine-3-acetic acid and N-benzylethylamine were used as raw materials for synthesis, white solid powder, yield 35.6%. m.p. 180-182° C., ESI-MS m/z: 452[M+H]$^+$, $^1$H NMR(CDCl$_3$, 400 MHz)δ: 1.05(t, 1.5H, J=7.00 Hz), 1.13(t, 1.5H, J=7.00 Hz), 2.44(s, 1.5H), 2.45(s, 1.5H), 3.27(q, 1H, J=7.00 Hz), 3.46(q, 1H, J=7.00 Hz), 4.05(s, 1H), 4.15(s, 1H), 4.43(s, 1H), 4.61(s, 1H), 6.73-6.88(m, 4H), 7.22-7.24(dd, 1H, J=7.00 Hz, 1.96 Hz), 7.28-7.35(m, 1H), 7.36-7.53(m, 2H), 7.56-7.60(m, 1H), 7.75(d, 1H, J=1.96 Hz), 8.10-8.11(d, 1H, J=7.00 Hz).

Example 20

N-ethyl-N-(2-pyridinylmethyl)-2-(3,4-dichlorophenyl)-7-methylimidazo[1,2-a]pyridine-3-acetamide.hydrochloride (Compound 8)

According to the method of Example 14, 2-(3,4-dichlorophenyl)-7-methylimidazo[1,2-a]pyridine-3-acetic acid and N-(2-pyridinylmethyl)ethylamine were used as raw materials for synthesis, white solid powder, yield 75.5%. m.p. 217-220° C., ESI-MS m/z: 454[M+H]$^+$, $^1$H NMR(DMSO-d$_6$, 400 MHz)δ: 0.99(t, 1.5H, J=7.00 Hz), 1.25(t, 1.5H, J=7.00 Hz), 2.57(s, 1.5H), 2.60(s, 1.5H), 3.33(q, 1H, J=7.00 Hz), 3.65(q, 1H, J=7.00 Hz), 4.56(s, 1H), 4.59(s, 1H), 4.78(s, 1H), 4.86(s, 1H), 7.40-7.53(m, 1H), 7.54-7.68(m, 2H), 7.78-7.81(m, 1H), 7.89(s, 1H), 7.91-7.95(m, 1H), 8.62-8.67(m, 2H), 8.84-8.86 (m, 2H).

Example 21

N-ethyl-N-(3-pyridinylmethyl)-2-(3,4-dichlorophenyl)-7-methylimidazo[1,2-a]pyridine-3-acetamide.hydrochloride (Compound 9)

According to the method of Example 14, 2-(3,4-dichlorophenyl)-7-methylimidazo[1,2-a]pyridine-3-acetic acid and N-(3-pyridinylmethyl)ethylamine were used as raw materials for synthesis, to obtain white solid powder, yield 70.8%. m.p. 245-248° C., ESI-MS m/z: 454[M+H]$^+$, $^1$H NMR(DMSO-d$_6$, 400 MHz)δ: 1.06(t, 0.7H, J=7.00 Hz), 1.25(t, 2.3H, J=7.00 Hz), 2.58(s, 3H), 3.34(q, 0.5H, J=7.00 Hz), 3.58(q, 1.5H, J=7.00 Hz), 4.45(s, 0.5H), 4.57(s, 1.5H), 4.70(s, 1.5H), 4.92 (s, 0.5H), 7.44-7.47(d, 1H, J=7.00 Hz), 7.56(dd, 0.2H, J=8.40 Hz, 1.96 Hz), 7.63(dd, 0.8H, J=8.40 Hz, 2.24 Hz), 7.80(s, 1H), 7.86(d, 0.2H, J=2.24 Hz), 7.87(d, 0.8H, J=1.96 Hz), 7.90(m, 1H), 7.94(d, 1H, J=8.40 Hz), 8.30-8.31(m, 1H), 8.74-8.77(m, 1H), 8.79(d, 1H, J=7.00 Hz), 8.82(m, 1H).

Example 22

N-ethyl-N-(4-pyridinylmethyl)-2-(3,4-dichlorophenyl)-7-methylimidazo[1,2-a]pyridine-3-acetamide.hydrochloride (Compound 10)

According to the method of Example 14, 2-(3,4-dichlorophenyl)-7-methylimidazo[1,2-a]pyridine-3-acetic acid and N-(4-pyridinylmethyl)ethylamine were used as raw materials for synthesis, to obtain white solid powder, yield 72.1%. m.p. 250-252° C., ESI-MS m/z: 454[M+H]$^+$, $^1$H NMR(DMSO-d$_6$, 400 MHz)δ: 1.09(t, 0.7H, J=7.00 Hz), 1.25(t, 2.3H, J=7.00 Hz), 2.57(s, 2.3H), 2.58(s, 0.7H), 3.38(q, 0.5H, J=7.00 Hz), 3.62(q, 1.5H, J=7.00 Hz), 4.32(s, 0.5H), 4.62(s, 1.5H), 4.79(s, 1.5H), 5.02(s, 0.5H), 7.41-7.43(m, 1H), 7.63-7.66(dd, 1H, J=8.40 Hz, 2.24 Hz), 7.79(s, 1H), 7.84-7.87(m, 2H), 7.89-7.90(d, 1H, J=2.24 Hz), 7.96-7.98(d, 1H, J=8.40 Hz), 8.69-8.77(m, 1H), 8.80-8.84(m, 2H).

Example 23

N-(2-methoxyethyl)-N-(2-pyridinylmethyl)-2-(3,4-dichlorophenyl)-7-methylimidazo[1,2-a]pyridine-3-acetamide.hydrochloride (Compound 11)

According to the method of Example 14, 2-(3,4-dichlorophenyl)-7-methylimidazo[1,2-a]pyridine-3-acetic acid and N-(2-pyridinylmethyl)-2-methoxyethylamine were used as raw materials for synthesis, to obtain light yellow solid powder, yield 68.6%. m.p. 236-238° C., ESI-MS m/z: 484[M+H]$^+$, $^1$H NMR(DMSO-d$_6$, 400 MHz)δ: 2.57(s, 2H), 2.60(s, 1H), 3.16(s, 1H), 3.27(s, 2H), 3.40(t, 0.7H, J=4.76 Hz), 3.47 (t, 0.7H, J=4.76 Hz), 3.60(t, 1.3H, J=4.76 Hz), 3.84(t, 1.3H, J=4.76 Hz), 4.56(s, 0.7H), 4.66(s, 1.3H), 4.84(s, 1.3H), 4.93 (s, 0.7H), 7.43-7.50(m, 1H), 7.62-7.65(dd, 1H, J=8.40 Hz, 2.24 Hz), 7.69-7.81(m, 2H), 7.88-7.90(d, 1H, J=8.40 Hz), 7.92-7.93(d, 1H, J=2.24 Hz), 7.95(s, 1H), 8.62-8.78(m, 2H), 8.76-8.84(m, 1H).

Example 24

N-(2-methoxyethyl)-N-(3-pyridinylmethyl)-2-(3,4-dichlorophenyl)-7-methylimidazo[1,2-a]pyridine-3-acetamide.hydrochloride (Compound 12)

According to the method of Example 14, 2-(3,4-dichlorophenyl)-7-methylimidazo[1,2-a]pyridine-3-acetic acid and N-(3-pyridinylmethyl)-2-methoxyethylamine were used as raw materials for synthesis, to obtain white solid powder, yield 74.4%. m.p. 235-237° C., ESI-MS m/z: 484[M+H]$^+$, $^1$H NMR(DMSO-d$_6$, 400 MHz)δ: 2.58(s, 3H), 3.20(s, 0.3H), 3.26(s, 2.7H), 3.57(t, 2H, J=4.76 Hz), 3.76(t, 2H, J=4.76 Hz), 4.43(s, 0.2H), 4.62(s, 1.8H), 4.74(s, 1.8H), 4.97(s, 0.2H), 7.47-7.48(d, 1H, J=7.00 Hz), 7.61(dd, 1H, J=8.4 Hz, 2.24 Hz), 7.8(s, 1H), 7.87-7.88(m, 1H), 7.91-7.92(d, 1H, J=2.24 Hz), 7.95-7.97(d, 1H, J=8.40 Hz), 8.27-8.29(m, 1H), 8.66-8.68(d, 1H, J=7.00 Hz), 8.75-8.79(m, 2H).

Example 25

N-benzyl-N-ethyl-2-(4-methylphenyl)-7-methylimidazo[1,2-a]pyridine-3-acetamide (Compound 13)

According to the method of Example 13, 2-(4-methylphenyl)-7-methylimidazo[1,2-a]pyridine-3-acetic acid and N-benzyl-2-methoxyethylamine were used as raw materials for synthesis, to obtain yellow solid powder, yield 54.6%. m.p. 220-222° C., ESm/z: 398[M+H]$^+$, $^1$H NMR(CDCl$_3$, 400 MHz)δ: 1.14(t, 1.5H, J=7.00 Hz), 1.17(t, 1.5H, J=7.00 Hz), 2.36(s, 1.5H), 2.37(s, 1.5H), 2.52(s, 1.5H), 2.54(s, 1.5H), 3.35(q, 1H, J=7.00 Hz), 3.52(q, 1H, J=7.00 Hz), 4.15(s, 1H), 4.24(s, 1H), 4.57(s, 1H), 4.61(s, 1H), 7.05-7.19(m, 1H), 7.22-7.36(m, 9H), 7.47-7.62(m, 1H), 8.13-8.29(m, 1H).

Example 26

N-ethyl-N-(2-pyridinylmethyl)-2-(4-methylphenyl)-7-methylimidazo[1,2-a]pyridine-3-acetamide.hydrochloride (Compound 14)

According to the method of Example 14, 2-(4-methylphenyl)-7-methylimidazo[1,2-a]pyridine-3-acetic acid and N-(2-pyridinylmethyl)ethylamine were used as raw materials for synthesis, to obtain white solid powder, yield 71.3%. m.p. 218-220° C., ESI-MS m/z: 399[M+H]$^+$, 1H NMR(DMSO-d6, 400 MHz)δ: 1.00(t, 1.5H, J=7.00 Hz), 1.25(t, 1.5H, J=7.00 Hz), 2.39(s, 1.5H), 2.43(s, 1.5H), 2.57(s, 1.5H), 2.60 (s, 1.5H), 3.34(q, 1H, J=7.00 Hz), 3.66(q, 1H, J=7.00 Hz), 4.51(s, 1H), 4.55(s, 1H), 4.83(s, 1H), 4.88(s, 1H), 7.41-7.43 (m, 1H), 7.46-7.56(m, 4H), 7.77-7.79(m, 2H), 7.92-7.94(m, 1H), 8.24(s, 1H), 8.68-8.73(m, 1H), 8.82-8.90(m, 1H).

Example 27

N-ethyl-N-(3-pyridinylmethyl)-2-(4-methylphenyl)-7-methylimidazo[1,2-a]pyridine-3-acetamide.hydrochloride (Compound 15)

According to the method of Example 14, 2-(4-methylphenyl)-7-methylimidazo[1,2-a]pyridine-3-acetic acid and N-(3-pyridinylmethyl)ethylamine were used as raw materials for synthesis, to obtain white solid powder, yield 56.7%. m.p. 251-253° C., ESI-MS m/z: 399[M+H]$^+$, $^1$H NMR(DMSO-d$_6$, 400 MHz)δ: 1.06(t, 0.7H, J=7.00 Hz), 1.22(t, 2.3H, J=7.00 Hz), 2.41(s, 0.7H), 2.42(s, 2.3H), 2.58(s, 3H), 3.37(q, 0.5H, J=7.00 Hz), 3.54(q, 1.5H, J=7.00 Hz), 4.36(s, 0.5H), 4.48(s, 1.5H), 4.67(s, 1.5H), 4.87(s, 0.5H), 7.38-7.40(m, 1H), 7.42-7.52(m, 4H), 7.77(s, 1H), 8.02-8.16(m, 1H), 8.70-8.77(m, 4H).

Example 28

N-ethyl-N-(4-pyridinylmethyl)-2-(4-methylphenyl)-7-methylimidazo[1,2-a]pyridine-3-acetamide.hydrochloride (Compound 16)

According to the method of Example 14, 2-(4-methylphenyl)-7-methylimidazo[1,2-a]pyridine-3-acetic acid and N-(4-pyridinylmethyl)ethylamine were used as raw materials for synthesis, to obtain white solid powder, yield 49.8%. m.p. 253-255° C., ESI-MS m/z: 399[M+H]$^+$, $^1$H NMR(DMSO-d$_6$, 400 MHz)δ: 1.10(t, 0.8H, J=7.00 Hz), 1.23(t, 2.2H, J=7.00 Hz), 2.40(s, 0.8H), 2.43(s, 2.2H), 2.58(s, 2.2H), 2.59(s, 0.8H), 3.40(q, 0.5H, J=7.00 Hz), 3.60(q, 1.5H, J=7.00 Hz), 4.23(s, 0.5H), 4.54(s, 1.5H), 4.76(s, 1.5H), 4.97(s, 0.5H), 7.38-7.42(m, 2H), 7.42-7.44(m, 1H), 7.45-7.54(m, 4H), 7.76-7.79(m, 1H), 8.75-8.76(m, 1H), 8.78-8.80(m, 2H).

Example 29

N-(2-methoxyethyl)-N-(2-pyridinylmethyl)-2-(4-methylphenyl)-7-methylimidazo[1,2-a]pyridine-3-acetamide.hydrochloride (Compound 17)

According to the method of Example 14, 2-(4-methylphenyl)-7-methylimidazo[1,2-a]pyridine-3-acetic acid and N-(2-pyridinylmethyl)-2-methoxyethylamine were used as raw materials for synthesis, to obtain light yellow solid powder, yield 43.7%. m.p. 239-240° C., ESI-MS m/z: 429[M+H]$^+$, $^1$H NMR(DMSO-d$_6$, 400 MHz)δ: 2.42(s, 1.2H), 2.43(s, 1.8H), 2.57(s, 1.8H), 2.60(s, 1.2H), 3.17(s, 1.2H), 3.27(s, 1.8H), 3.40(t, 0.8H, J=4.76 Hz), 3.48(t, 0.8H, J=4.76 Hz), 3.57(t, 1.2H, J=4.76 Hz), 3.80(t, 1.2H, J=4.76 Hz), 4.51(s, 0.8H), 4.60(s, 1.2H), 4.79(s, 1.2H), 4.91(s, 0.8H), 7.40-7.43 (m, 1H), 7.45-7.56(m, 4H), 7.76(s, 1H), 7.77-7.88(m, 2H), 8.65-8.70(m, 2H), 8.78-8.80(m, 1H).

Example 30

N-(2-methoxyethyl)-N-(3-pyridinylmethyl)-2-(4-methylphenyl)-7-methylimidazo[1,2-a]pyridine-3-acetamide.hydrochloride (Compound 18)

According to the method of Example 14, 2-(4-methylphenyl)-7-methylimidazo[1,2-a]pyridine-3-acetic acid and N-(3-pyridinylmethyl)-2-methoxyethylamine were used as raw materials for synthesis, to obtain white solid powder, yield 57.3%. m.p. 224-226° C., ESI-MS m/z: 429[M+H]$^+$, $^1$H NMR(DMSO-d$_6$, 400 MHz)δ: 2.42(s, 0.3H), 2.43(s, 2.7H), 2.58(s, 2.7H), 2.59(s, 0.3H), 3.22(s, 0.3H), 3.27(s, 2.7H), 3.56(t, 2H, J=4.76 Hz), 3.76(t, 2H, J=4.76 Hz), 4.36(s, 0.2H), 4.60(s, 1.8H), 4.75(s, 1.8H), 4.98(s, 0.2H), 7.38-7.43(m, 1H), 7.46-7.55(m, 4H), 7.78(s, 1H), 7.90-7.93(m, 1H), 8.31-8.33(m, 1H), 8.66-8.72(m, 1H), 8.77-8.80(m, 2H).

Example 31

N-benzyl-N-ethyl-2-(4-methoxyphenyl)-7-methylimidazo[1,2-a]pyridine-3-acetamide (Compound 19)

According to the method of Example 13, 2-(4-methoxyphenyl)-7-methylimidazo[1,2-a]pyridine-3-acetic acid and N-benzylethylamine were used as raw materials for synthesis, to obtain yellow solid powder, yield 50.0%. m.p. 175-178° C., ESI-MS m/z: 414[M+H]$^+$, $^1$H NMR(CDCl$_3$, 400 MHz) δ: 1.14(t, 1.2H, J=7.00 Hz), 1.17(t, 1.8H, J=7.00 Hz), 2.53(s, 1.5H), 2.55(s, 1.5H), 3.32(q, 0.7H, J=7.00 Hz), 3.54(q, 1.3H, J=7.00 Hz), 3.84(s, 1.5H), 3.86(s, 1.5H), 4.10(s, 1H), 4.19(s, 1H), 4.5(s, 0.8H), 4.6(s, 1.2H), 6.92-6.94(m, 1H), 7.00-7.36(m, 9H), 7.55-7.70(m, 1H), 8.14-8.27(m, 1H).

Example 32

N-ethyl-N-(2-pyridinylmethyl)-2-(4-methoxyphenyl)-7-methylimidazo[1,2-a]pyridine-3-acetamide.hydrochloride (Compound 20)

According to the method of Example 14, 2-(4-methoxyphenyl)-7-methylimidazo[1,2-a]pyridine-3-acetic acid and N-(2-pyridinylmethyl)ethylamine were used as raw materials for synthesis, to obtain light yellow solid powder, yield 59.1%. m.p. 228-230° C., ESI-MS m/z: 415[M+H]$^+$, $^1$H NMR(DMSO-d$_6$, 400 MHz)δ: 1.01(t, 1.5H, J=7.00 Hz), 1.25(t, 1.5H, J=7.00 Hz), 2.57(s, 1.5H), 2.59(s, 1.5H), 3.36(q, 1H, J=7.00 Hz), 3.66(q, 1H, J=7.00 Hz), 3.86(s, 1.5H), 3.87(s, 1.5H), 4.49(s, 1H), 4.53(s, 1H), 4.82(s, 1H), 4.87(s, 1H), 7.15-7.21(m, 2H), 7.40-7.53(m, 2H), 7.58-7.61(m, 2H), 7.75-7.77(m, 1H), 7.91-7.94(m, 1H), 8.20(s, 1H), 8.68-8.71(m, 1H), 8.80-8.87(m, 1H).

Example 33

N-ethyl-N-(3-pyridinylmethyl)-2-(4-methoxyphenyl)-7-methylimidazo[1,2-a]pyridine-3-acetamide.hydrochloride (Compound 21)

According to the method of Example 14, 2-(4-methoxyphenyl)-7-methylimidazo[1,2-a]pyridine-3-acetic acid and N-(3-pyridinylmethyl)ethylamine were used as raw materials for synthesis, to obtain white solid powder, yield 59.1%. m.p. 230-232° C., ESI-MS m/z: 415[M+H]$^+$, $^1$H NMR(DMSO-d$_6$, 400 MHz)δ: 1.08(t, 0.7H, J=7.00 Hz), 1.23(t, 2.3H, J=7.00 Hz), 2.58(s, 3H), 3.38(q, 0.5H, J=7.00 Hz), 3.56(q, 1.5H, J=7.00 Hz), 3.86(s, 3H), 4.33(s, 0.5H), 4.48(s, 1.5H), 4.70(s, 1.5H), 4.91(s, 0.5H), 7.13-7.15(m, 1H), 7.19-7.21(m, 2H), 7.44-7.48(m, 1H), 7.55-7.57(m, 2H), 7.77(s, 1H), 7.86-7.90(m, 1H), 8.18-8.30(m, 1H), 8.71-8.76(m, 1H), 8.77-8.81(m, 1H).

Example 34

N-ethyl-N-(4-pyridinylmethyl)-2-(4-methoxyphenyl)-7-methylimidazo[1,2-a]pyridine-3-acetamide.hydrochloride (Compound 22)

According to the method of Example 14, 2-(4-methoxyphenyl)-7-methylimidazo[1,2-a]pyridine-3-acetic acid and N-(4-pyridinylmethyl)ethylamine were used as raw materials for synthesis, to obtain yellow solid powder, yield 66.5%. m.p. 239-242° C., ESI-MS m/z: 415[M+H]$^+$, $^1$H NMR(DMSO-d$_6$, 400 MHz)δ: 1.11(t, 0.7H, J=7.00 Hz), 1.24(t, 2.3H, J=7.00 Hz), 2.57(s, 2.3H), 2.58(s, 0.7H), 3.42(q, 0.5H, J=7.00 Hz), 3.61(q, 1.5H, J=7.00 Hz), 3.86(s, 0.7H), 3.87(s, 2.3H), 4.21(s, 0.5H), 4.55(s, 1.5H), 4.78(s, 1.5H), 5.02(s, 0.5H), 7.11-7.13(m, 1H), 7.20-7.23(m, 2H), 7.41-7.47(m, 2H), 7.58-7.60(m, 2H), 7.76(s, 1H), 7.86-7.87(m, 1H), 8.75-8.77(m, 1H), 8.82-8.84(m, 1H).

Example 35

N-(2-methoxyethyl)-N-(2-pyridinylmethyl)-2-(4-methoxyphenyl)-7-methylimidazo[1,2-a]pyridine-3-acetamide.hydrochloride (Compound 23)

According to the method of Example 14, 2-(4-methoxyphenyl)-7-methylimidazo[1,2-a]pyridine-3-acetic acid and N-(2-pyridinylmethyl)-2-methoxyethylamine were used as raw materials for synthesis, to obtain yellow solid powder, yield 62.4%. m.p. 214-216° C. (decomposition), ESI-MS m/z: 445[M+H]$^+$, $^1$H NMR(DMSO-d$_6$, 400 MHz)δ: 2.56(s, 2H), 2.59(s, 1H), 3.18(s, 1H), 3.28(s, 2H), 3.42(t, 0.7H, J=4.76 Hz), 3.50(t, 0.7H, J=4.76 Hz), 3.60(t, 1.3H, J=4.76 Hz), 3.83(t, 1.3H, J=4.76 Hz), 3.87(s, 3H), 4.48(s, 0.7H), 4.62(s, 1.3H), 4.86(s, 1.3H), 4.93(s, 0.7H), 7.14-7.17(m, 1H), 7.19-7.21(m, 2H), 7.42-7.46(m, 1H), 7.49-7.54(m, 1H), 7.57-7.61(m, 2H), 7.70(m, 1H), 7.76(s, 1H), 8.68-8.72(m, 2H), 8.77-8.79(m, 1H).

Example 36

N-(2-methoxyethyl)-N-(3-pyridinylmethyl)-2-(4-methoxyphenyl)-7-methylimidazo[1,2-a]pyridine-3-acetamide.hydrochloride (Compound 24)

According to the method of Example 14, 2-(4-methoxyphenyl)-7-methylimidazo[1,2-a]pyridine-3-acetic acid and N-(3-pyridinylmethyl)-2-methoxyethylamine were used as raw materials for synthesis, to obtain white solid powder, yield 48.5%. m.p. 243-245° C., ESI-MS m/z: 445[M+H]$^+$, $^1$H NMR(DMSO-d$_6$, 400 MHz)δ: 2.58(s, 3H), 3.23(s, 0.3H), 3.27(s, 2.7H), 3.55(t, 2H, J=4.76 Hz), 3.74(t, 2H, J=4.76 Hz), 3.87(s, 3H), 4.33(s, 0.2H), 4.56(s, 1.8H), 4.72(s, 1.8H), 4.94(s, 0.2H), 7.20-7.22(m, 2H), 7.45-7.46(m, 1H), 7.56-7.58(m, 2H), 7.76(s, 1H), 7.80(m, 1H), 8.19(m, 1H), 8.62-8.64(m, 1H), 8.69-8.73(m, 2H).

Example 37

N-(2-methoxyethyl)-N-(2-morpholinylethyl)-2-(4-methylphenyl)-7-methylimidazo[1,2-a]pyridine-3-acetamide.hydrochloride (Compound 25)

According to the method of Example 14, 2-(4-methylphenyl)-7-methylimidazo[1,2-a]pyridine-3-acetic acid and N-(2-methoxyethyl)-2-morpholine-ethylamine were used as raw materials for synthesis, to obtain white solid powder, yield 22.6%. m.p. 165-167° C., ESI-MS m/z: 451[M+H]$^+$, $^1$H NMR(DMSO-d$_6$, 400 MHz) δ: 2.41(s, 3H), 2.57(s, 3H), 3.06-3.12(m, 2H), 3.26(s, 3H), 3.36(m, 2H), 3.55-3.57(m, 4H), 3.68(m, 2H), 3.78(m, 2H), 3.95(m, 4H), 4.58(s, 2H), 7.43-7.45(m, 2H), 7.52(m, 1H), 7.52-7.54(m, 2H), 7.75(s, 1H), 9.26-9.27(m, 1H).

Example 38

N-(2-methoxyethyl)-N-(2-morpholinylethyl)-2-(4-methylphenyl)-6-methylimidazo[1,2-a]pyridine-3-acetamide.hydrochloride (Compound 26)

According to the method of Example 14, 2-(4-methylphenyl)-6-methylimidazo[1,2-a]pyridine-3-acetic acid and N-(2-methoxyethyl)-2-morpholine-ethylamine were used as raw materials for synthesis, to obtain white solid powder, yield 34.2%. m.p. 245-247° C., ESI-MS m/z: 451 [M+H]$^+$, $^1$H NMR(DMSO-d$_6$, 400 MHz)δ: 2.41(s, 3H), 2.48(s, 3H), 3.05-3.10(m, 2H), 3.25(s, 3H), 3.36-3.38(m, 2H), 3.55-3.60 (m, 4H), 3.69(m, 2H), 3.80(m, 2H), 3.95(m, 4H), 4.58(s, 2H), 7.44-7.53(m, 4H), 7.87-7.90(m, 2H), 9.46(s, 1H).

Example 39

N-ethyl-N-(4-pyridinylmethyl)-2-(4-methylphenyl)-6-methylimidazo[1,2-a]pyridine-3-acetamide.hydrochloride (Compound 27)

According to the method of Example 14, 2-(4-methylphenyl)-6-methylimidazo[1,2-a]pyridine-3-acetic acid and N-(4-pyridinylmethyl)ethylamine were used as raw materials for synthesis, to obtain light yellow solid powder, yield 78.9%. m.p. 222-224° C., ESI-MS m/z: 399[M+H]$^+$, $^1$H NMR(DMSO-d$_6$, 400 MHz)δ: 1.11(t, 0.7H, J=7.00 Hz), 1.24 (t, 2.3H, J=7.00 Hz), 2.41(s, 0.7H), 2.43(s, 2.3H), 2.46(s, 2.3H), 2.47(s, 0.7H), 3.43(q, 0.5H, J=7.00 Hz), 3.63(q, 1.5H, J=7.00 Hz), 4.24(s, 0.5H), 4.56(s, 1.5H), 4.78(s, 1.5H), 5.02 (s, 0.5H), 7.39-7.43(m, 1H), 7.47-7.55(m, 4H), 7.85-7.89(m, 2H), 7.91-7.93(m, 1H), 8.75(s, 1H), 8.80-8.83(m, 2H).

Example 40

N-ethyl-N-(4-pyridinylmethyl)-2-(4-chlorophenyl)-6-methylimidazo[1,2-a]pyridine-3-acetamide.hydrochloride (Compound 28)

According to the method of Example 14, 2-(4-chlorophenyl)-6-methylimidazo[1,2-a]pyridine-3-acetic acid and N-(4-pyridinylmethyl)ethylamine were used as raw materials for synthesis, to obtain white solid powder, yield 32.9%. m.p. 229-231° C., ESI-MS m/z: 420[M+H]$^+$, $^1$H NMR(DMSO-d$_6$, 400 MHz)δ: 1.11(t, 0.6H, J=7.00 Hz), 1.25(t, 2.4H, J=7.00 Hz), 2.47(s, 2.4H), 2.49(s, 0.6H), 3.42(q, 0.4H, J=7.00 Hz), 3.63(q, 1.6H, J=7.00 Hz), 4.25(s, 0.4H), 4.56(s, 1.6H), 4.78(s, 1.6H), 5.01(s, 0.4H), 7.55-7.58(m, 1H), 7.65-7.76(m, 4H), 7.84-7.86(m, 2H), 7.90-7.92(m, 1H), 8.71(s, 1H), 8.80-8.84 (m, 2H).

Example 41

Screening of Drugs Using Translocation Protein (TSPO, 18KD) and Radioligand ($^3$H-PK11195) Binding Test Model Experimental Mechanism:

In the present test, TSPO protein separated and purified from rat heart was used as screening target, via competitive binding test with radioligand ($^3$H-PK11195), to screen TSPO ligand compounds.

Experimental Materials:

Animals: Wister rats (220-260 g, male and female), purchased from the Laboratory Animal Center of the Academy of Military Medical Sciences.

Instruments: high speed refrigerated centrifuge (H1ACH1 20PR-5), ultraspeed refrigerated centrifuge (H1ACH1 SCP85H), homogenizer (ULTRA-TURRAXT25), UV-250 ultraviolet spectrophotometer (Shimadzu Company, Japan), multihead suction filter (self-made), LS6500 type scintillation counter (Beckman Company), 49 type glass fiber filter membrane (Shanghai Yuguang Scavenging Material Integrated Corporation)

Reagents: $^3$H-PK11195(5 μCi(83.4Ci/mmol)) and scintillation solution were purchased from PE company, PK11195, R05-4864, Polyethyleneimine (PEI), bovine serum albumin (BSA), protease inhibitor (PMSF) were purchased from Sigma Company, Folin-phenol reagent was purchased from Huaweikeyi Company, Tris-HCl Buffer pH7.4(50 mM Tris-HCl Buffer, 1 mM EDTA, 5 mM MgCl$_2$, 1 mM PMSF, 0.1% NaN$_3$, 3 μg/mL protease inhibitor), other reagents were all analytically pure (Beijing Chemical Reagents Company).

Test drugs: Compounds 1-28(see: Table 1), total 28 compounds

Experimental Methods:

1) Preparation of Rat Heart TSPO Membrane Protein:

Wister rats, 220-260 g, female and male, were sacrificed by decapitation and the rat heart were rapidly separated, weighed and to which homogenized in 10 times volume of Tris-HCl buffer solution (50 mM Tris-HCl, 5 mM MgCl$_2$, 1 mM EDTA, 0.5% (W/V) BSA, 1 mM PMSF, 3 μg/ml proteinase inhibitor, 0.1% NaN$_3$, 0.32M sucrose, pH 7.4) at 15,000 rpm for 30 s, total 5 times. The homogenate was centrifuged under 1000×g for 10 minutes and the supernatant was then centrifuged under 30000×g for 20 minutes. The precipitate was collected, and resuspended with 10 times volume of Tris-HCl buffer solution (pH 7.4) relative to the original weight, then centrifuged under 30000×g for 20 minutes. The precipitate was washed with the same buffer solution, centrifuged under 30000×g for 20 minutes and the precipitate was suspended with the above buffer solution. After sub-packaged (the whole operation procedures were performed under ice bath), the product was stored at −80° C.

2) Measurement of Protein Content (Folin Method)

100 μL of sample, which contained BSA 5-100 μg (used for making standard curve) or a sample to be tested, and complemented with water when less than 100 μL, was added to 100 μL with reagent A ((1) 0.2N NaOH solution containing 4% sodium carbonate and 0.2% sodium tartrate (Na$_2$C$_4$H$_9$O$_6$.2H$_2$O), (2) 4% copper sulfate (CuSO$_4$.5H$_2$O) water solution, homogeneously mixing (1) and (2) in proportion of 100:1 to obtain the reagent A, which should be used within one day after being prepared), mixed and reacted at room temperature for 10 min, then added with 20 μL reagent B (Folin phenol reagent, final concentration: 1N), mixed immediately, placed in 50° C. water bath, incubated for 15 min, 200 μL of the mixture was taken and measured to determine optical density value using trace multichannel scanning optical densitometer, wavelength 690 nm, optical path 0.6 cm, and 100 μL of H$_2$O was used as blank control to replace the sample.

3) Competitive Binding Test of Drug to the Receptor (Rat Heart TSPO) and Radioligand ($^3$H-PK11195):

| Total binding tube | Test tube | Non-specific binding tube |
|---|---|---|
| ○○ | ○○○○○○○○○○ | ○○ |
| ○○ | ○○○○○○○○○○ | ○○ |

(1) tubes were placed in reaction condition of 30° C.

(2) all tubes were added with 20 µg of receptor protein in order;

(3) the test tubes were added in order with 20 µL of drugs in certain concentrations;

(4) the non-specific binding tubes were added with 20 µL of non-tagged ligand (PK11195), the final concentration of the non-tagged ligand was 0.1 mM, pre-reacted for 30 min;

(5) all tubes were added in order with 25 µL $^3$H-PK11195, the final concentration of the labeled ligand was 1.5 nM;

(6) Tris-HCl Buffer pH7.4 was used to complement the reaction volumes of all tubes to reach 200 µL;

(7) the reaction was performed under 30° C. reaction condition for 1 h;

(8) Then samples were applied to 49-type glass fibre filter, vacuum suction filtered, then washed with 2 ml ice-cold Tris-HCl buffer solution (50 mM Tris-HCl buffer solution, 1 mM EDTA, 5 mM $MgCl_2$, 1 mM PMSF, 0.1% $NaN_3$, 3 µg/ml proteinase inhibitor, pH 7.4). The filter was dried and placed in a scintillation vial with 1 ml of scintillation fluid. The radio-activity was measured by a scintillation counter.

Experimental Results:

(1) The TSPO separated and purified from rat heart was used as drug-screening target, via the binding test with radio-ligand ($^3$H-PK11195), 29 compounds were screened, in which Ro5-4864 was used as positive control, and the 29 compounds were subjected to competitive binding test respectively. The screening results show that in comparison with the positive control, the screened compounds have competitive binding results as shown in Table 2:

TABLE 2

Screening results of TSPO ligand compounds (n = 6 times)

| Compound | Inhibition rate (%) | | |
|---|---|---|---|
| | $1 \times 10^{-5}$M | $1 \times 10^{-7}$M | $1 \times 10^{-9}$M |
| RO5-4864 (positive control) | 100 | 82 | 57 |
| Compound 1 | 100 | 87 | 12 |
| Compound 2 | 100 | 59 | 0 |
| Compound 3 | 100 | 25 | 0 |
| Compound 4 | 100 | 50 | 0 |
| Compound 5 | 100 | 43 | 0 |
| Compound 6 | 70 | 0 | 0 |
| Compound 7 | 99 | 72 | 10 |
| Compound 8 | 100 | 89 | 30 |
| Compound 9 | 86 | 8 | 0 |
| Compound 10 | 100 | 85 | 23 |
| Compound 11 | 100 | 65 | 29 |
| Compound 12 | 80 | 20 | 0 |
| Compound 13 | 97 | 89 | 42 |
| Compound 14 | 97 | 66 | 14 |
| Compound 15 | 90 | 15 | 0 |
| Compound 16 | 72 | 41 | 0 |
| Compound 17 | 83 | 9 | 0 |
| Compound 18 | 69 | 32 | 0 |
| Compound 19 | 94 | 76 | 0 |
| Compound 20 | 61 | 63 | 0 |
| Compound 21 | 43 | 11 | 0 |
| Compound 22 | 63 | 9 | 4 |
| Compound 23 | 85 | 2 | 3 |
| Compound 24 | 17 | 3 | 0 |
| Compound 25 | 31 | 0 | 0 |
| Compound 26 | 48 | 1 | 0 |
| Compound 27 | 91 | 65 | 0 |
| Compound 28 | 84 | 33 | 0 |

Compounds 1, 7, 8, 10, 11, 13 and 14 that had higher binding activity as shown in the above screening test were further subjected to radioligand competitive binding test with 9 gradient concentrations in $10^{-3}$-$10^{-12}$ M, and their $IC_{50}$ and $K_i$ values were calculated by plotting and fitting. The results are shown in Table 3.

TABLE 3

The activities of some active compounds to the separated and purified TSPO

| Compound | $IC_{50}$ (nM) | $K_i$(nM) |
|---|---|---|
| Ro 5-4864 | 0.68 | 0.29 |
| Compound 1 | 16.86 | 7.17 |
| Compound 7 | 115.60 | 49.19 |
| Compound 8 | 21.94 | 9.34 |
| Compound 10 | 26.05 | 11.09 |
| Compound 11 | 15.64 | 6.66 |
| Compound 13 | 6.99 | 2.97 |
| Compound 14 | 91.02 | 38.73 |

Below Examples 42-47 are animal behavior tests, including: mice open field spontaneous locomotor activity test, mice tail suspension test, mice elevated plus maze test, and rat forced swim test.

Animals: ICR mice (source: Beijing Vital Laboratory Animal Technology Company), male, body weight 20-24 g; SD rats (source: Beijing Vital Laboratory Animal Technology Company), male, SPF grade, body weight 180-220 g.

Drugs: Compound 8(8[#], YL-IPA08), Compound 10(10[#], YL-IPA10), Compound 11(11[#], YL-IPA11) and Compound 13(13[#], YL-IPA13), Diazepam (DZP), Desipramine (DMI); administration manner: oral administration (po); intraperitoneal administration (ip).

Statistic methods: All data were expressed as mean±SEM. Except that PK11195 antagonism test was determined by two-way analysis of variance, all other tests were determined by one-way analysis of variance, and Bonferroni test was used for group comparison.

Example 42

Mice Spontaneous Locomotor Activity in Mice

Experimental mechanism: the aim was to observe the effects of drugs on central nervous excitation, so as to exclude false positive reactions of anxiolytic or antidepressant effects caused by central nervous excitation. After administration, apparent central nervous excitation or inhibition effects were observed, when the observed indexes were equivalent to those of the blank control group, there were not apparent central nervous excitation or inhibition effects; when the observed indexes were significantly higher than those of the blank control, there were apparent central nervous excitation effects, on the contrary, there were central nervous inhibition effects.

1) Experimental device: the mice open field box was a colorless transparent organic glass box (30×36×25 cm), which bottom surface was divided into 9 lattices.

2) Experimental operation: Compound 8(8[#], YL-IPA08), Compound 10(10[#], YL-IPA10), Compound 11(11[#], YL-IPA11) and Compound 13(13[#], YL-IPA13) (separately having three dose groups of 0.03, 0.3, 3 mg/kg) and blank control (distilled water, DW) were administered intragastrically, and the test started after 55 min. During test, the mice were placed in the central area of the open field spontaneous locomotor activity observation box, started timing immediately, the spontaneous activities of mice within 5 min were recorded artificially (observation indexes: number of rearings, number of crossings).

Figure 2:
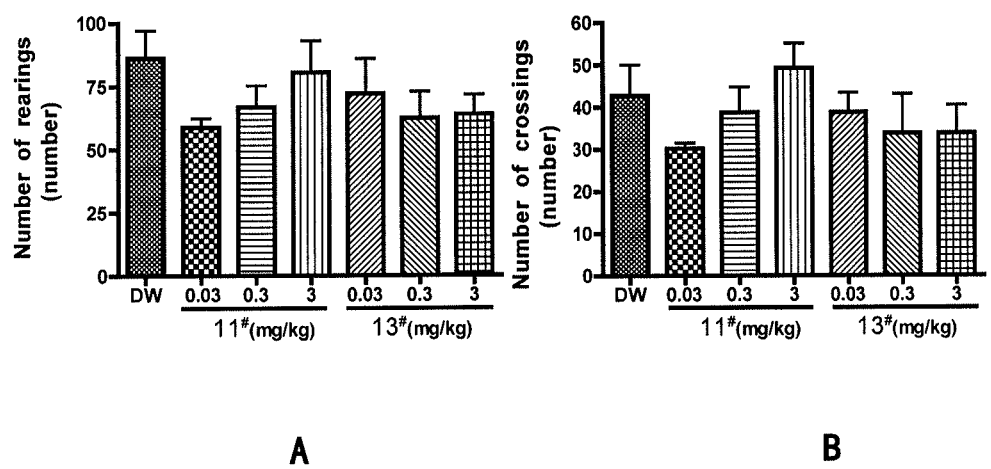
FIG. 2: Effects of Example Compounds 11 and 13 on open field spontaneous locomotor activity in mice. The results are shown in $\bar{x}\pm s$, n=5.

3) Experimental results: as shown in FIG. 1 and FIG. 2.

The above two indexes of Compound 8 and 10, in doses of 0.03, 0.3, 3 mg/kg, were equivalent to those of the control, which showed Compound 8 and 10 did not have apparent central nervous excitation or inhibition effects;

Compound 11 was equivalent to the control in the two indexes only when the dose was 3 mg/kg, and was lower than the control when the dose was 0.03 and 0.3 mg/kg, which suggested it could have central nervous inhibition effects;

Compound 13 was apparently lower than the control (DW) when the dose was 0.03, 0.3, 3 mg/kg, and the activity declined with the increase of dose, which suggested that it had certain central nervous inhibition effects.

Example 43

Mice Tail Suspension Test

Experimental mechanism: mice tail suspension test was an acute behavioral despair model established by Steru et al (1985). In this model, mice struggled at full stretch to escape discomfort posture, and the motionless state intermittently appeared due to invalid struggle was deemed as "despair state", while typical antidepressant (such as tricyclics, SSRI) all could significantly reduce mice immobility time. This model was easy in operation, with good predictability, and was the most popular model for screening antidepressants.

1) Experimental device: an experimental frame with spacing boards which dividing the experimental frame into 2 experimental chambers (25×25×35 cm). A clamp is mounted on a through cross rod in the chamber.

2) Experimental Methods

Male Kunming mice weighing 20-25 g. The mice were intragastrically administered with Compound 8, vehicle (distilled water, DW) or positive control drug (desipramine, DMI). After 1 h, wrap adhesive tape around the mouse's tail three quarters of the distance from the base of the tail and then suspend the animals by passing the suspension hook through the adhesive tape 5 cm above the table. The duration of immobility in the last 4 min of total 6 min test was recorded.

Compound 8 was dissolved in distilled water, had doses of 0.1, 0.3, 1 mg/kg, respectively, and administration in a volume of 10 mL/kg; desipramine had dose of 30 mg/kg was the minimum effective dose to generate antidepression activity of desipramine, which was the minimum effective dose to generate antidepression activity.

Statistic method: All data were expressed as mean±SEM. The results were determined by one-way analysis of variance, and Bonferroni test was used for group comparison.

Figure 3:
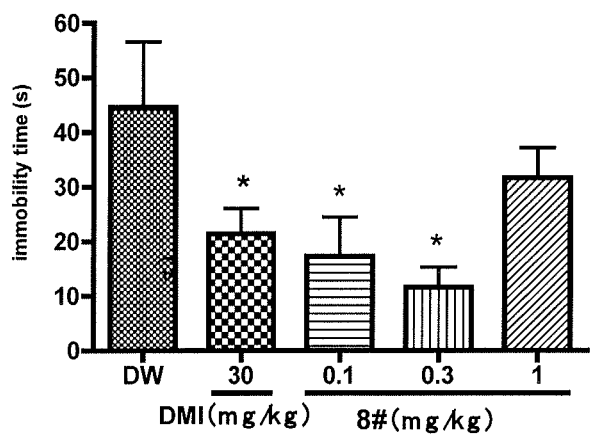
FIG. 3: Effects of Example Compound 8 on immobility time in tail suspension test in mice. The results are shown in $\bar{x}\pm s$, n=8-9, *$P<0.05$ in comparison with DW group.

3) Experimental results, as shown in FIG. 3.

It can be seen in FIG. 3, the mice with intragastric administration of Compound 8 exhibited antidepression activity superior to the positive control desipramine (DMI) in tail suspension test, and the relation between potency and dose was in reverse U type distribution.

Example 44

Blocking Effects of TSPO Antagonist PK11195 on Compound 8(YL-IPA08) Antidepressant Activity The optimum dose (0.1 mg/kg) of YL-IPA08 in antidepressant effect of mice in tail suspension model was used to perform drug antagonism test, and the method was identical to that of Example 43, except that PK11195 group and PK11195+Compound 8 antagonism group with single intraperitoneal injection (ip) were added, wherein the antagonism group was administered by intraperitoneal injection with PK11195 simultaneously when Compound 8 was intragastrically administered.

Statistic method: the results were expressed in mean±SEM. The result was determined by two-way analysis of variance, and Bonferroni test was used for group comparison.

Figure 4:
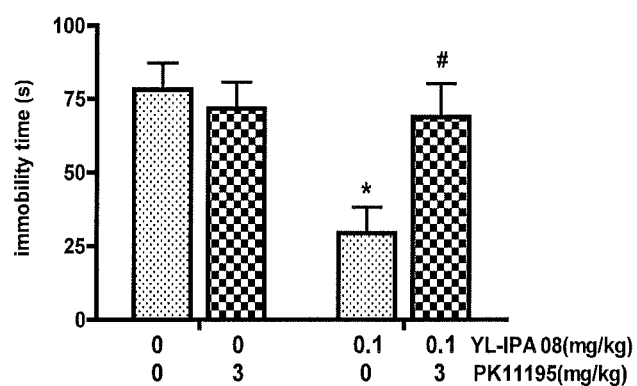
FIG. 4: Effects of PK11195 on the antidepressant-like effect of Compound 8 in mice tail suspension test. The results are shown in $\bar{x}\pm s$, n=8-11, *$P<0.05$ in comparison with DW group; #$p<0.05$ in comparison with Compound 8 group.

The results were shown in FIG. 4, in comparison with the control, single administration of TSPO selective antagonist PK11195(3 mg/kg, ip) had no significant influence on immobility time in mice tail suspension test; while in comparison with the group with single administration of YL-IPA08(0.1 mg/kg), the PK11195+YL-IPA08 group increased the immobility time ($P<0.05$), which suggested that the antidepressant effect of YL-IPA08 could be antagonized by TSPO antagonist PK11195 in mice tail suspension test.

Example 45

Mice Elevated Plus Maze Test

Experimental mechanism: In this test, animals were placed in the central area of maze, then the time and number the animals separately entered open arm and close arm within a certain time period were observed. Since this has certain novelty and certain threatening for the animal, the animals would generate curiosity and anxiety reaction. When having high anxiety level, the animals would leave the open arm and stayed in the close arm, otherwise the animals would stay in the open arm for more time with increased number of exploring open arm. Typical anxiolytic drugs (such as benzodiazepines) can selectively increase the animal's behavior of exploring open arm without influencing total number and total time of entering arms.

1) Experimental device: mice elevated plus maze was a cross shape colorless transparent organic glass box, arm length 30 cm, width 5 cm, the close arm had sides surrounded with side wall with height of 15 cm, and opened top; the open arm was total open; the joint area (central area) for the open and close arms was 5×5 cm. The total device was elevated with a distance of 45 cm from the ground.

2) Experimental operation: male Kunming mice, body weight 20-25 g, were separately administered intragastrically with Compound 8 or the blank control distilled water (DW) and observed after 1 h, or administered intraperitoneally with positive control drug diazepam (DZP) and observed after 30 min. During observation, place the animal in the central platform, facing an open arm. Observe the animal for 5 min. The numbers of entries into open arms and closed arms as well as the time spent in open arms or closed arms were recorded.

Compound 8(8#, YL-IPA08) was separately at three doses of 0.1, 0.3, 1 mg/kg; and 2 mg/kg was the minimum effective dose for generating anxiolytic-like effects of diazepam.

Observation indexes: percentage of number of entering open arm=number of entering arms/(number of entering open arm+number of entering close arm)

Percentage of time spent in open arm=time spent in open arm/ (time spent in open arm+time spent in close arm)

Observation indexes: entering open and close arms refers to all four paws entering the arms.

Figure 5:
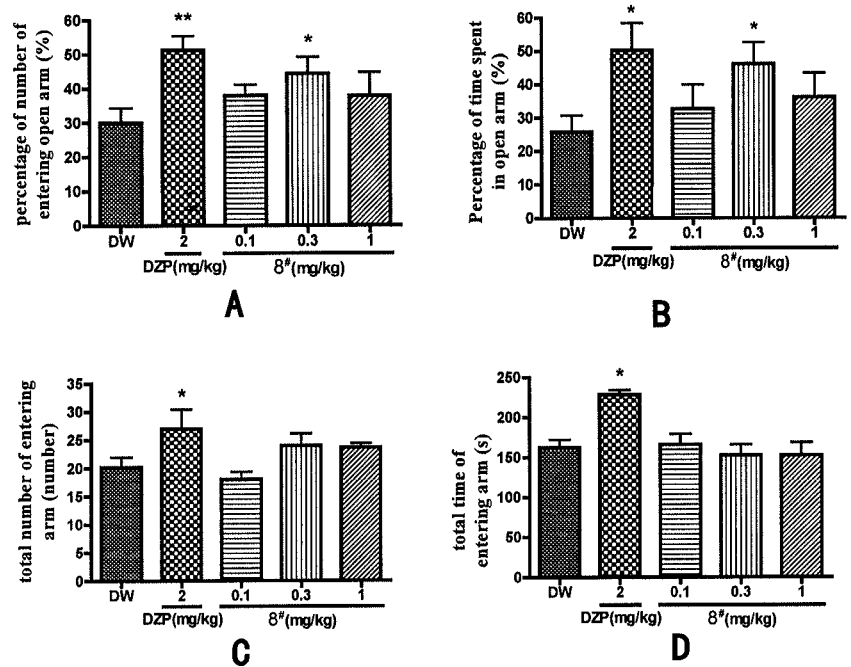
FIG. 5: Effects of Example Compound 8 on behavior of mice in elevated plus maze test. The results are shown in $\bar{x}\pm s$, n=6, *$P<0.05$, **$P<0.01$ in comparison with DW group.
Figure 6:
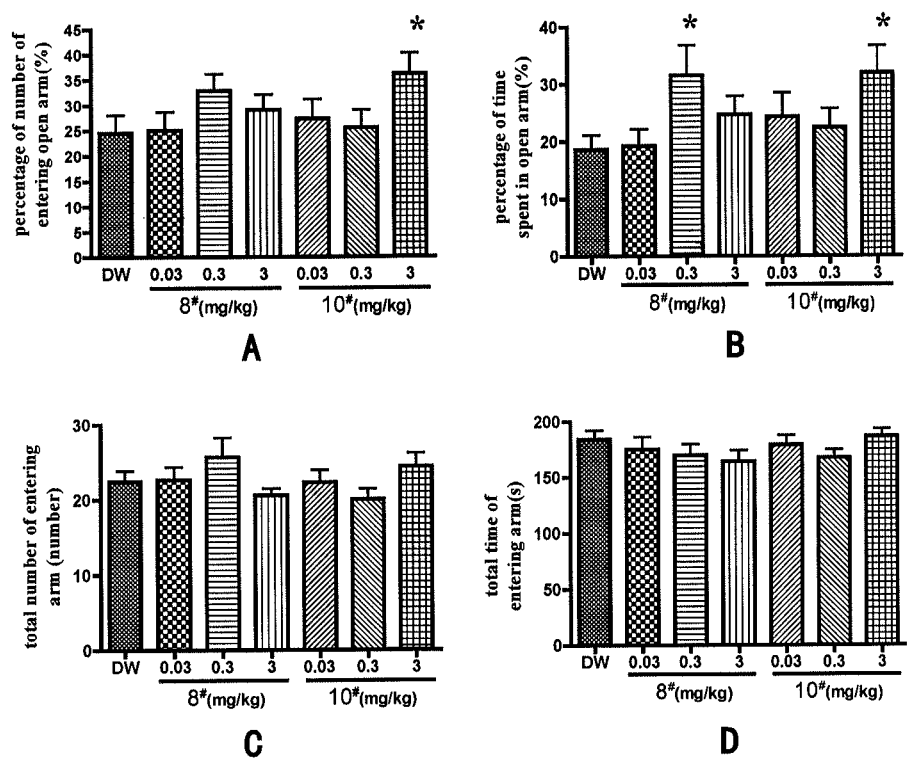
FIG. 6: Effects of Example Compounds 8 and 10 on behavior of mice in elevated plus maze test. The results are shown in $\bar{x}\pm s$, n=9-10, *$P<0.05$ in comparison with DW group.
Figure 7:
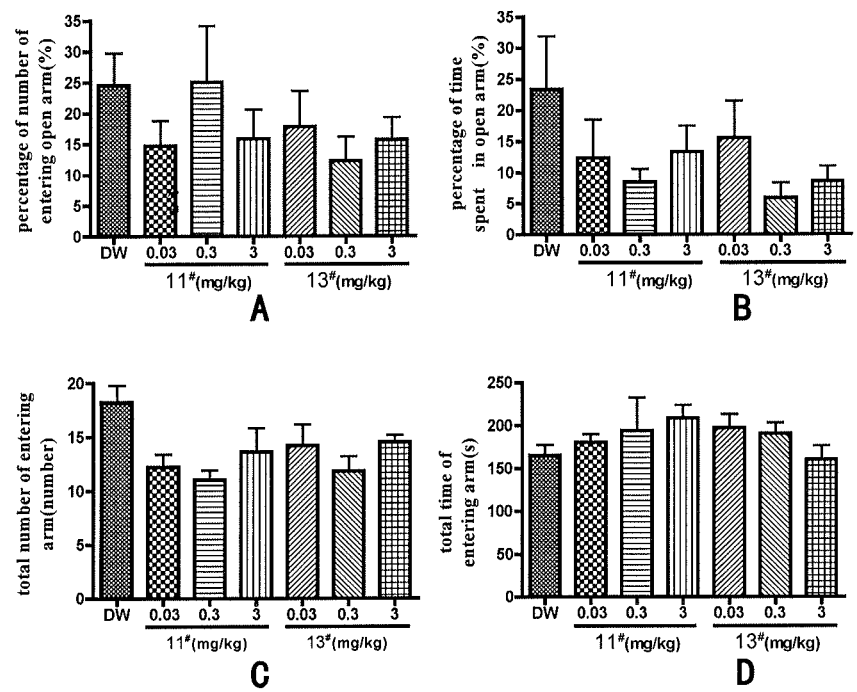
FIG. 7: Effects of Example Compounds 11 and 13 on behavior of mice in elevated plus maze test. The results are shown in $\bar{x}\pm s$, n=5.

Experimental results: the result of Compound 8 was shown in FIG. 5. Compound 10 (10#, YL-IPA10), Compound 11 (11#, YL-IPA11) and Compound 13 (13#, YL-IPA13) were subjected to the same test, and the results were shown in FIG. 6, FIG. 7.

It can be seen from the figures that in the mice elevated plus maze test, the intragastric administration of Compound 8 at doses of 0.1, 0.3, 1 mg/kg could relatively increase the number and time the mice spent entering in open arm, and did not influence the total number and total time the mice entering open arm and close arm. In comparison with the blank control distilled water (DW) group, the 0.3 mg/kg group showed significant difference in the percentage of number of entering open arm and the percentage of time spent in open arm, which suggested that Compound 8 had significant anxiolytic effects at dose of 0.3 mg/kg.

Compound 10, was equivalent to the control at dose of 0.03, 0.3 mg/kg, while significant higher than the control at dose of 3 mg/kg. This suggested that Compound 10 had significant anxiolytic effects, and its anxiolytic onset dose was higher than that of Compound 8.

Compound 11, was only equivalent to the control in the percentage of number of entering open arm at dose of 0.03 mg/kg, and was significantly lower in indexes at other doses in comparison with the control, which suggested that Compound 11 had no significant anxiolytic effects in this model.

Compound 13, was significantly lower than the control in all indexes at dose of 0.03, 0.3, 3 mg/kg, which suggested that Compound 13 had no significant anxiolytic effects in this model.

Example 46

Rat Forced Swim Test

The method established by Porsolt [Eur J. Pharmacol. 1978, 47(4): 379-91.] was used, in which rat swim tank was a round glass with height of 40 cm, diameter of 20 cm, and water depth of 25 cm, the water temperature was 28° C. 24 h before the test, the rats one-by-one were placed in the swim tank, swam 15 min in advance, then dried and put back in the original rearing cage. 60 min before the test, they were separately administered (p.o.) with YL-IPA08, DLX or DW at different doses. During the test, the rats were placed again in the swim tank, and timing and observation started and continued for 5 min, the accumulated immobility time was recorded using stopwatch. The standard for judging motionless was that animal stopped struggle in water and was in floating state, or had little limb motion to keep head float.

Statistic method: the results were expressed in mean±SEM. The result was determined by one-way analysis of variance, and Bonferroni test was used for group comparison.

Figure 8:
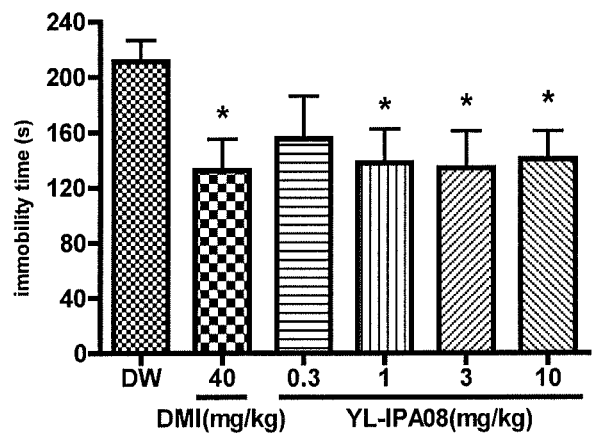
FIG. 8: Effects of Example Compound 8 on immobility time in forced swim test in rats. The results are shown in $\bar{x}\pm s$, n=8, *$P<0.05$ in comparison with DW group.

Experimental results: in comparison with the blank control, YL-IPA08(1, 3, 10 mg·kg$^{-1}$) showed increased immobility time significantly shortened swim immobility time (all had P<0.05) (FIG. 8), and was equivalent to the positive drug DMI (40 mg·kg$^{-1}$). This suggested that YL-IPA08 had antidepressant effect in this model. The results are shown in FIG. 8.

Example 47

Measurement of Contents of Rat Serum Neurosteroid Pregnenolone (PREG) and Progesterone (PROG)

24 male SD rats were randomly divided into 4 groups, separately being YL-IPA08(1, 3, 10 mg/kg) groups and distilled water (DW) group, were immediately sacrificed by decapitation after the end of rat forced swim test (same as the method of Example 46), their trunk blood samples were taken, stood at room temperature for 3 h, centrifuged (3000 rpm, 20 min) to take serum, stored at −20° C. The contents of rat serum PREG and PROG were separately measured using ELISA or radio-immunoassay kit.

The measurement of PREG used ELISA kit from German DRG Company, and the operation was performed according to its specification. The measurement of PROG used $^{125}$I-PROG radio-immunoassay kit from Beijing Beifang Biological Science and Technology Institute, and the operation was performed according to its specification.

Statistic methods: the results were expressed in average value ±standard error, one-way analysis of variance was used for the test results, and Bonferroni test was used for group comparison.

Figure 9:
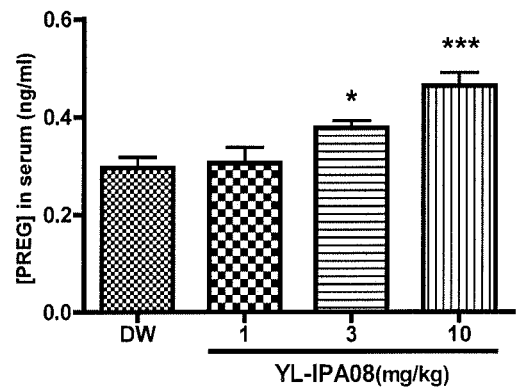
FIG. 9: Effects of Example Compound 8 on serum pregnenolone (PREG) in forced swim rats. The results are shown in $\bar{x}\pm s$, n=6, *$P<0.05$ in comparison with DW group.
Figure 10:
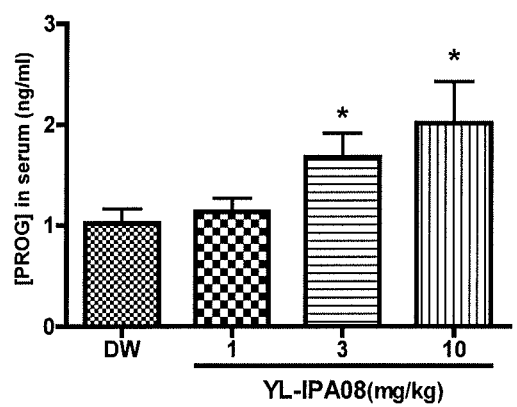
FIG. 10: Effects of Example Compound 8 on serum progesterone (PROG) in forced swim rats. The results are shown in $\bar{x}\pm s$, n=6, *$P<0.05$ in comparison with DW group.

Experimental results: the results showed that after the administration (p.o.) of YL-IPA08 for 60 min, the contents of rat serum PREG and PROG increased in dose-dependent manner, in comparison with the blank control group, significant differences were observed in doses of 3 mg/kg and 10 mg/kg, and the results were shown in FIG. 9, FIG. 10. This suggested that the antiadepression behavior effects of YL-IPA08 could be related to the increase of neurosteroid in vivo.

Although the present invention is described in details in the specific examples, those skilled in the art would understand those details could be modified or replaced under the teachings as disclosed, and all of these modifications fall within to the protection scope of the present invention. The protection scope of the present invention was determined by the attached claims and any equivalents thereof.

What is claimed is:

1. A compound of Formula I, its tautomer, its racemic or optical isomer, its pharmaceutically acceptable salt (which is water soluble), or its solvate,

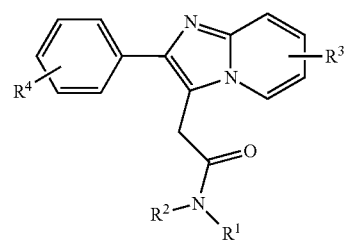

wherein:
R$^1$ is selected from ethyl, propyl, butyl, and methoxyethyl;
R$^2$ is selected from 2-pyridinylmethyl, 3-pyridinylmethyl, 4-pyridinylmethyl, 2-morpholinylethyl, and 3-morpholinylpropyl;
R$^3$ is 6-methyl or 7-methyl;
R$^4$ is 1-3 substituents selected from H, halogen, alkyl, substituted hydrocarbonyl, alkenyl, substituted alkenyl, phenyl, substituted phenyl, heteroaryl, substituted heteroaryl, C$_1$-C$_6$ alkoxyl, C$_5$-C$_{10}$ aryloxy, substituted aryloxy, C$_1$-C$_6$ alkylamino, C$_5$-C$_1$ arylamino, substituted arylamino, di-(C$_1$-C$_6$ alkyl)amino, di-(C$_5$-C$_{10}$ aryl)amino, di-(substituted aryl)amino, C$_{1-10}$ hydrocarbonylacyloxy, C$_{6-10}$ arylacyloxy, C$_{1-10}$ hydrocarbonylacylamino, C$_{6-10}$ arylacylamino, carboxyl, C$_{1-10}$ hydrocarbonyloxyformyl, C$_{6-10}$ aryloxyformyl, aminoformyl, C$_{1-10}$ hydrocarbonylaminoformyl, or C$_{6-10}$ arylaminoformyl; wherein the heteroaromatic cycle is a monocyclic or fused aromatic hydrocarbonyl having 1-3 heteroatoms selected from N, O or S, each of the substituents of groups having substituents is selected from halogen, hydroxyl, cyano, nitro, $C_{1-6}$ alkyl, $C_{1-6}$ alkoxyl, $C_{1-6}$ alkylthio, mono- or di- or tri-halogenated $C_{1-6}$ alkyl, amino, $C_{1-6}$ alkylamino, $C_{1-10}$ hydrocarbonylacyloxy, $C_{1-10}$ hydrocarbonylacylamino, $C_{6-10}$ arylacyloxy, and $C_{6-10}$ arylacylamino.

2. The compound of Formula I according to claim 1, its tautomer, its racemic or optical isomer, its pharmaceutically acceptable salt, or its solvate, wherein $R^3$ is at 4-, 5-, 6-, or 7-position of imidazo[1,2-a]pyridine ring; $R^4$ is at ortho-, meta- or para-position of benzene ring.

3. The compound of Formula I according to claim 1, its tautomer, its racemic or optical isomer, its pharmaceutically acceptable salt, or its solvate, wherein, $R^3$ and $R^4$ are independently selected from F, Cl, Br, I, $C_1$-$C_6$ alkyl, $C_1$-$C_3$ alkoxylethyl, and $C_1$-$C_6$ alkoxyl, wherein $R^3$ has 1-2 substituents, and $R^4$ has 1-3 substituents.

4. The compound of Formula I according to claim 1, its tautomer, its racemic or optical isomer, its pharmaceutically acceptable salt, or its solvate, wherein $R^1$ is ethyl or methoxyethyl.

5. A compound of Formula I, its tautomer, its racemic or optical isomer, its pharmaceutically acceptable salt (which is water soluble), or its solvate,

I wherein:
$R^1$ is selected from ethyl, propyl, butyl, and methoxyethyl;
$R^2$ is selected from 2-pyridinylmethyl, 3-pyridinylmethyl, 4-pyridinylmethyl, 2-morpholinylethyl, and 3-morpholinylpropyl;
$R^3$ is 1-2 substituents selected from H, halogen, alkyl, substituted hydrocarbonyl, alkenyl, substituted alkenyl, phenyl, substituted phenyl, heteroaryl, substituted heteroaryl, $C_1$-$C_6$ alkoxyl, $C_5$-$C_{10}$ aryloxy, substituted aryloxy, $C_1$-$C_6$ alkylamino, $C_5$-$C_{10}$ arylamino, substituted arylamino, di-($C_1$-$C_6$ alkyl)amino, di-($C_5$-$C_1$ aryl)amino, di-(substituted aryl)amino, $C_{1-10}$ hydrocarbonylacyloxy, $C_{6-10}$ arylacyloxy, $C_{1-10}$ hydrocarbonylacylamino, $C_{6-10}$ arylacylamino, carboxyl, $C_{1-10}$ hydrocarbonyloxyformyl, $C_{6-10}$ aryloxyformyl, aminoformyl, $C_{1-10}$ hydrocarbonylaminoformyl, or $C_{6-10}$ arylaminoformyl; wherein the heteroaromatic cycle is a monocyclic or fused aromatic hydrocarbonyl having 1-3 heteroatoms selected from N, O or S, each of the substituents of groups having substituents is selected from halogen, hydroxyl, cyano, nitro, $C_{1-6}$ alkyl, $C_{1-6}$ alkoxyl, $C_{1-6}$ alkylthio, mono- or di- or tri-halogenated $C_{1-6}$ alkyl, amino, $C_{1-6}$ alkylamino, $C_{1-10}$ hydrocarbonylacyloxy, $C_{1-10}$ hydrocarbonylacylamino, $C_{6-10}$ arylacyloxy, and $C_{6-10}$ arylacylamino; and
$R^4$ is 4-chloro, 3,4-dichloro, 4-methyl, or 4-methoxy.

6. The compound of Formula I according to claim 5, its tautomer, its racemic or optical isomer, its pharmaceutically acceptable salt, or its solvate, wherein $R^3$ is at 4-, 5-, 6-, or 7-position of imidazo[1,2-a]pyridine ring; $R^4$ is at ortho-, meta- or para-position of benzene ring.

7. The compound of Formula I according to claim 6, its tautomer, its racemic or optical isomer, its pharmaceutically acceptable salt, or its solvate, wherein, $R^3$ and $R^4$ are independently selected from F, Cl, Br, I, $C_1$-$C_6$ alkyl, $C_1$-$C_3$ alkoxylethyl, and $C_1$-$C_6$ alkoxyl, wherein $R^3$ has 1-2 substituents, and $R^4$ has 1-3 substituents.

8. The compound of Formula I according to claim 6, its tautomer, its racemic or optical isomer, its pharmaceutically acceptable salt, or its solvate, wherein $R^1$ is ethyl or methoxyethyl.

9. A compound, its tautomer, its racemic or optical isomer, its pharmaceutically acceptable salt, or its solvate, which is selected from the following compounds:

N-benzyl-N-ethyl-2-(4-chlorophenyl)-7-methylimidazo[1,2-a]pyridine-3-acetamide;

N-ethyl-N-(2-pyridinylmethyl)-2-(4-chlorophenyl)-7-methylimidazo[1,2-a]pyridine-3-acetamide.hydrochloride;

N-ethyl-N-(3-pyridinylmethyl)-2-(4-chlorophenyl)-7-methylimidazo[1,2-a]pyridine-3-acetamide.hydrochloride;

N-ethyl-N-(4-pyridinylmethyl)-2-(4-chlorophenyl)-7-methylimidazo[1,2-a]pyridine-3-acetamide.hydrochloride;

N-(2-methoxyethyl)-N-(2-pyridinylmethyl)-2-(4-chlorophenyl)-7-methylimidazo[1,2-a]pyridine-3-acetamide.hydrochloride;

N-(2-methoxyethyl)-N-(3-pyridinylmethyl)-2-(4-methylphenyl)-7-methylimidazo[1,2-a]pyridine-3-acetamide.hydrochloride;

N-benzyl-N-ethyl-2-(3,4-dichlorophenyl)-7-methylimidazo[1,2-a]pyridine-3-acetamide;

N-ethyl-N-(2-pyridinylmethyl)-2-(3,4-dichlorophenyl)-7-methylimidazo[1,2-a]pyridine-3-acetamide.hydrochloride;

N-ethyl-N-(3-pyridinylmethyl)-2-(3,4-dichlorophenyl)-7-methylimidazo[1,2-a]pyridine-3-acetamide-hydrochloride;

N-ethyl-N-(4-pyridinylmethyl)-2-(3,4-dichlorophenyl)-7-methylimidazo[1,2-a]pyridine-3-acetamide-hydrochloride;

N-(2-methoxyethyl)-N-(2-pyridinylmethyl)-2-(3,4-dichlorophenyl)-7-methylimidazo[1,2-a]pyridine-3-acetamide-hydrochloride;

N-(2-methoxyethyl)-N-(3-pyridinylmethyl)-2-(3,4-dichlorophenyl)-7-methylimidazo[1,2-a]pyridine-3-acetamide.hydrochloride;

N-benzyl-N-ethyl-2-(4-methylphenyl)-7-methylimidazo[1,2-a]pyridine-3-acetamide;

N-ethyl-N-(2-pyridinylmethyl)-2-(4-methylphenyl)-7-methylimidazo[1,2-a]pyridine-3-acetamide.hydrochloride;

N-ethyl-N-(3-pyridinylmethyl)-2-(4-methylphenyl)-7-methylimidazo[1,2-a]pyridine-3-acetamide.hydrochloride;

N-ethyl-N-(4-pyridinylmethyl)-2-(4-methylphenyl)-7-methylimidazo[1,2-a]pyridine-3-acetamide.hydrochloride;

N-(2-methoxyethyl)-N-(2-pyridinylmethyl)-2-(4-methylphenyl)-7-methylimidazo[1,2-a]pyridine-3-acetamide.hydrochloride;

N-(2-methoxyethyl)-N-(3-pyridinylmethyl)-2-(4-methylphenyl)-7-methylimidazo[1,2-a]pyridine-3-acetamide.hydrochloride;

N-benzyl-N-ethyl-2-(4-methoxyphenyl)-7-methylimidazo[1,2-a]pyridine-3-acetamide;

N-ethyl-N-(2-pyridinylmethyl)-2-(4-methoxyphenyl)-7-methylimidazo[1,2-a]pyridine-3-acetamide.hydrochloride;

N-ethyl-N-(3-pyridinylmethyl)-2-(4-methoxyphenyl)-7-methylimidazo[1,2-a]pyridine-3-acetamide-hydrochloride;

N-ethyl-N-(4-pyridinylmethyl)-2-(4-methoxyphenyl)-7-methylimidazo[1,2-a]pyridine-3-acetamide.hydrochloride;

N-(2-methoxyethyl)-N-(2-pyridinylmethyl)-2-(4-methoxyphenyl)-7-methylimidazo[1,2-a]pyridine-3-acetamide.hydrochloride;

N-(2-methoxyethyl)-N-(3-pyridinylmethyl)-2-(4-methoxyphenyl)-7-methylimidazo[1,2-a]pyridine-3-acetamide.hydrochloride;

N-(2-methoxyethyl)-N-(2-morpholinylethyl)-2-(4-methylphenyl)-7-methylimidazo[1,2-a]pyridine-3-acetamide.hydrochloride;

N-(2-methoxyethyl)-N-(2-morpholinylethyl)-2-(4-methylphenyl)-6-methylimidazo[1,2-a]pyridine-3-acetamide.hydrochloride;

N-ethyl-N-(4-pyridinylmethyl)-2-(4-methylphenyl)-6-methylimidazo[1,2-a]pyridine-3-acetamide.hydrochloride; and N-ethyl-N-(4-pyridinylmethyl)-2-(4-chlorophenyl)-6-methylimidazo[1,2-a]pyridine-3-acetamide.hydrochloride.

10. A pharmaceutical composition comprising at least one compound of Formula I according to claim 3, its tautomer, its racemic or optical isomer, its pharmaceutically acceptable salt, or its solvate, and optionally a pharmaceutically acceptable carrier or adjuvant.

11. The compound of Formula I according to claim 3, its racemic or optical isomer, its pharmaceutically acceptable salt, or its solvate, wherein $R^3$, $R^4$ are independently selected from F, Cl, methyl, ethyl, methoxyethyl, methoxy, and ethoxy.

12. The compound of Formula I according to claim 3, its racemic or optical isomer, its pharmaceutically acceptable salt, or its solvate, wherein $R^2$ is 2-pyridinylmethyl, 3-pyridinylmethyl, 4-pyridinylmethyl, or 2-morpholinylethyl.

13. A pharmaceutical composition, comprising at least one compound of Formula I according to claim 7, its tautomer, its racemic or optical isomer, its pharmaceutically acceptable salt, or its solvate, and optionally a pharmaceutically acceptable carrier or adjuvant.

14. The compound of Formula I according to claim 7, its racemic or optical isomer, its pharmaceutically acceptable salt, or its solvate, wherein $R^3$, $R^4$ are independently selected from F, Cl, methyl, ethyl, methoxyethyl, methoxy, and ethoxy.

15. The compound of Formula I according to claim 7, its racemic or optical isomer, its pharmaceutically acceptable salt, or its solvate, wherein $R^2$ is 2-pyridinylmethyl, 3-pyridinylmethyl, 4-pyridinylmethyl, or 2-morpholinylethyl.

16. A method for preparing the compound of Formula I, its tautomer, its racemic or optical isomer, its pharmaceutically acceptable salt, or its solvate according to claims 1, comprising the following steps:

a) converting an aromatic hydrocarbon compound of Formula VIII:

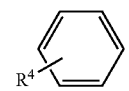

via Friedel-Crafts acetylation to form a ketone compound of Formula VII:

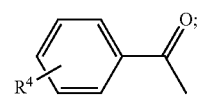

b) reacting the ketone compound VII with bromine under the catalysis of aluminum trichloride to form a bromide, not being separated, reacting with an aminopyridine compound of Formula VI,

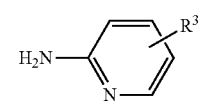

under heating and in the presence of an alkali or alkaline compound to form an imidazopyridine compound of Formula V:

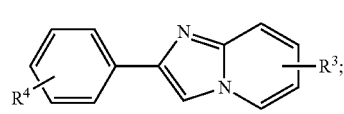

C) reacting the imidazopyridine compound V with dimethylamine and formaldehyde aqueous soltuion in acetic acid to form a Mannich base, separating via filtration, then reacting with iodomethane to form a quaternary ammonium salt of Formula IV:

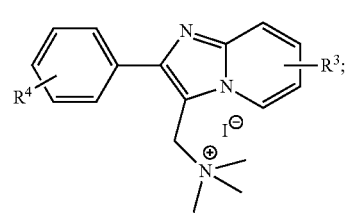

d) reacting the quaternary ammonium salt IV with a cyanide to form a corresponding nitrile, then hydrolyzing in the presence of a strong base, and acidifying to form a carboxylic compound of Formula II

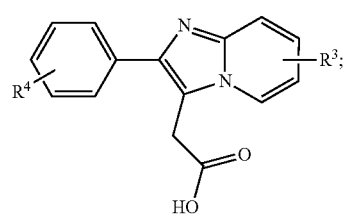

e) in the presence or absence of a catalyst, such as 4-dimethylaminopyridine, reacting the carboxylic compound of Formula II as obtained in step d) with an amine compound of Formula III in the presence of a condensing agent:

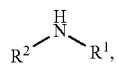

to obtain a compound of Formula I

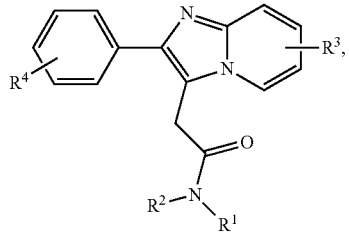

wherein:
R¹ is selected from ethyl, propyl, butyl, and methoxyethyl;
R² is selected from 2-pyridinylmethyl, 3-pyridinylmethyl, 4-pyridinylmethyl, 2-morpholinylethyl, and 3-morpholinylpropyl;
R³ is 6-methyl or 7-methyl:
R⁴ is 1-3 substituents selected from H, halogen, alkyl, substituted hydrocarbonyl, alkenyl, substituted alkenyl, phenyl, substituted phenyl, heteroaryl, substituted heteroaryl, $C_1$-$C_6$ alkoxyl, $C_5$-$C_{10}$ aryloxy, substituted aryloxy, $C_1$-$C_6$ alkylamino, $C_5$-$C_{10}$ arylamino, substituted arylamino, di-($C_5$-$C_{10}$ alkyl)amino, di-($C_5$-$C_{10}$ aryl)amino, di-(substituted aryl)amino, $C_1$-$C_{10}$ hydrocarbonylacyloxy, $C_6$-$C_{10}$ arylacyloxy, $C_1$-$C_{10}$ hydrocarbonylacylamino, $C_6$-$C_{10}$ arylacylamino, carboxyl, $C_1$-$C_{10}$ hydrocarbonyloxyformyl, $C_6$-$C_{10}$ aryloxyformyl, aminoformyl, $C_1$-$C_{10}$ hydrocarbonylaminoformyl, or $C_6$-$C_{10}$ arylaminoformyl; wherein the heteroaromatic cycle is a monocyclic or fused aromatic hydrocarbonyl having 1-3 heteroatoms selected from N, O or S, each of the substituents of groups having substituents is selected from halogen, hydroxyl, cyano, nitro, $C_1$-$C_6$ alkyl, $C_1$-$C_6$ alkoxyl, $C_1$-$C_6$ alkylthio, mono- or di- or tri-halogenated $C_1$-$C_6$ alkyl, amino, $C_1$-$C_6$ alkylamino, $C_1$-$C_{10}$ hydrocarbonylacyloxy, $C_1$-$C_{10}$ hydrocarbonylacylamino, $C_6$-$C_{10}$ arylacyloxy, and $C_6$-$C_{10}$ arylacylamino; or a tautomer, racemic or optical isomer, pharmaceutically acceptable salt (which is water soluble), or solvate thereof.

17. A method for preparing the compound of Formula I, its tautomer, its racemic or optical isomer, its pharmaceutically acceptable salt, or its solvate according to claim 1, comprising the following steps:
a) converting an aromatic hydrocarbon compound of Formula VIII:

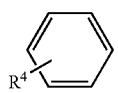

via Friedel-Crafts acetylation using succinic anhydride to form a ketonic acid compound of Formula VIII':

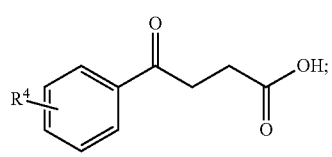

b) subjecting the above ketonic acid compound of Formula VIII' to bromination with bromine to form a brominated acid compound of Formula VII':

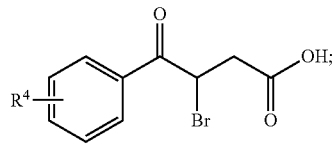

c) reacting the above brominated acid compound of Formula VII' with a chloroformate (such as ethyl chloroformate or isobutyl chloroformate) to form a mixed acid anhydride, then reacting with an amine of Formula III:

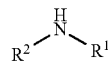

in the presence or absence of a catalyst, and in the presence of an alkali to form a bromonated amide compound of Formula II':

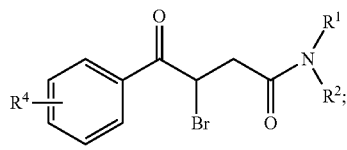

d) subjecting the above bromonated amide compound of Formula I1' and an aminopyridine compound of Formula VI:

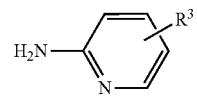

to condensation in the presence of an alkali to prepare a compound of Formula I:

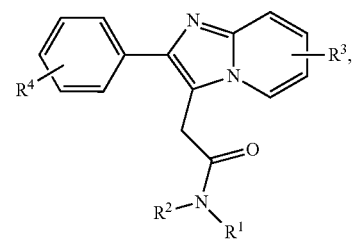

wherein:
R¹ is selected from ethyl, propyl, butyl, and methoxyethyl;
R² is selected from 2-pyridinylmethyl, 3-pyridinylmethyl, 4-pyridinylmethyl, 2-morpholinylethyl, and 3-morpholinylpropyl;
R³ is 6-methyl or 7-methyl:
R⁴ is 1-3 substituents selected from H, halogen, alkyl, substituted hydrocarbonyl, alkenyl, substituted alkenyl, phenyl, substituted phenyl, heteroaryl, substituted heteroaryl, $C_1$-$C_6$ alkoxyl, $C_5$-$C_{10}$ aryloxy, substituted aryloxy, $C_1$-$C_6$ alkylamino, $C_5$-$C_{10}$ arylamino, substituted arylamino, di-($C_5$-$C_{10}$ alkyl)amino, di-($C_5$-$C_{10}$ aryl)amino, di-(substituted aryl)amino, $C_1$-$C_{10}$ hydrocarbonylacyloxy, $C_6$-$C_{10}$ arylacyloxy, $C_1$-$C_{10}$ hydrocarbonylacylamino, $C_6$-$C_{10}$ arylacylamino, carboxyl, $C_1$-$C_{10}$ hydrocarbonyloxyformyl, $C_6$-$C_{10}$ aryloxyformyl, aminoformyl, $C_1$-$C_{10}$hydrocarbonylaminoformyl, or $C_6$-$C_{10}$ arylaminoformyl; wherein the heteroaromatic cycle is a monocyclic or fused aromatic hydrocarbonyl having 1-3 heteroatoms selected from N, O or S, each of the substituents of groups having substituents is selected from halogen, hydroxyl, cyano, nitro, $C_1$-$C_6$ alkyl, $C_1$-$C_6$ alkoxyl, $C_1$-$C_6$ alkylthio, mono- or di- or tri-halogenated $C_1$-$C_6$ alkyl, amino, $C_1$-$C_6$ alkylamino, $C_1$-$C_{10}$ hydrocarbonylacyloxy, $C_1$-$C_{10}$ hydrocarbonylacylamino, $C_6$-$C_{10}$ arylacyloxy, and $C_6$-$C_{10}$ arylacylamino; or a tautomer, racemic or optical isomer, pharmaceutically acceptable salt (which is water soluble), or solvate thereof.

18. A method of treating a translocator protein (TSPO)-associated condition selected from the group consisting of anxiety and depression comprising administering to a mammal in need thereof a therapeutically effective amount of a compound of Formula I:

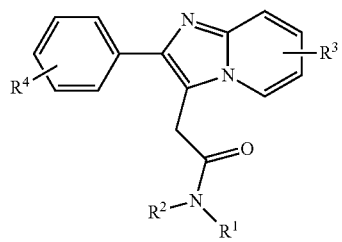

I wherein:
$R^1$ is selected from ethyl, propyl, butyl, and methoxyethyl;
$R^2$ is selected from, 2-pyridinylmethyl, 3-pyridinylmethyl, 4-pyridinylmethyl, 2-morpholinylethyl, and 3-morpholinylpropyl;
$R^3$, $R^4$ are independently selected from H, halogen, alkyl, substituted hydrocarbonyl, alkenyl, substituted alkenyl, phenyl, substituted phenyl, heteroaryl, substituted heteroaryl, $C_1$-$C_6$ alkoxyl, $C_5$-$C_{10}$ aryloxy, substituted aryloxy, $C_1$-$C_6$ alkylamino, $C_5$-$C_{10}$ arylamino, substituted arylamino, di-($C_5$-$C_{10}$ alkyl)amino, di-($C_5$-$C_{10}$ aryl)amino, di-(substituted aryl)amino, $C_1$-$C_{10}$ hydrocarbonylacyloxy, $C_6$-$C_{10}$ arylacyloxy, $C_1$-$C_{10}$ hydrocarbonylacylamino, $C_6$-$C_{10}$ arylacylamino, carboxyl, $C_1$-$C_{10}$ hydrocarbonyloxyformyl, $C_6$-$C_{10}$ aryloxyformyl, aminoformyl, $C_1$-$C_{10}$ hydrocarbonylaminoformyl, or $C_6$-$C_{10}$ arylaminoformyl; wherein the heteroaromatic cycle is a monocyclic or fused aromatic hydrocarbonyl having 1-3 heteroatoms selected from N, O or S, each of the substituents of groups having substituents is selected from halogen, hydroxyl, cyano, nitro, $C_1$-$C_6$ alkyl, $C_1$-$C_6$ alkoxyl, $C_1$-$C_6$ alkylthio, mono- or di- or tri-halogenated $C_1$-$C_6$ alkyl, amino, $C_1$-$C_6$ alkylamino, $C_1$-$C_{10}$ hydrocarbonylacyloxy, $C_1$-$C_{10}$ hydrocarbonylacylamino, $C_6$-$C_{10}$ arylacyloxy, and $C_6$-$C_{10}$ arylacylamino; or a tautomer, racemic or optical isomer, pharmaceutically acceptable salt, or solvate thereof.

19. The method according to claim 18 wherein the compound is a TSPO ligand.

* * * * *

UNITED STATES PATENT AND TRADEMARK OFFICE
CERTIFICATE OF CORRECTION

PATENT NO. : 8,980,887 B2  
APPLICATION NO. : 13/805967  
DATED : March 17, 2015  
INVENTOR(S) : Rifang Yang et al.

Page 1 of 1

It is certified that error appears in the above-identified patent and that said Letters Patent is hereby corrected as shown below:

In the Claims

In column 49, claim 16, line 64, after "solvate according to" replace "claims 1," with --claim 1,--.

Signed and Sealed this  
First Day of December, 2015

Michelle K. Lee  
*Director of the United States Patent and Trademark Office*